(12) United States Patent
Mori et al.

(10) Patent No.: US 8,980,431 B2
(45) Date of Patent: Mar. 17, 2015

(54) PRIMER COMPOSITION FOR OPTICAL ARTICLES AND OPTICAL ARTICLES

(75) Inventors: Katsuhiro Mori, Shunan (JP); Shunichiro Nakatsukasa, Shunan (JP)

(73) Assignee: Tokuyama Corporation, Yamaguchi (JP)

( * ) Notice: Subject to any disclaimer, the term of this patent is extended or adjusted under 35 U.S.C. 154(b) by 0 days.

(21) Appl. No.: 13/820,636

(22) PCT Filed: Sep. 9, 2011

(86) PCT No.: PCT/JP2011/070598
§ 371 (c)(1),
(2), (4) Date: Mar. 4, 2013

(87) PCT Pub. No.: WO2012/036084
PCT Pub. Date: Mar. 22, 2012

(65) Prior Publication Data
US 2013/0164540 A1 Jun. 27, 2013

(30) Foreign Application Priority Data
Sep. 13, 2010 (JP) ................. 2010-204655

(51) Int. Cl.
*G02B 1/04* (2006.01)
*G02B 1/12* (2006.01)
(Continued)

(52) U.S. Cl.
CPC . *G02B 1/10* (2013.01); *A61F 9/023* (2013.01);
*C08G 18/44* (2013.01); *C08K 3/22* (2013.01);
*C08K 2003/2237* (2013.01); *C08L 67/00*
(2013.01); *C08L 67/02* (2013.01); *C08L 69/00*
(2013.01); *C08L 75/00* (2013.01);
(Continued)

(58) Field of Classification Search
USPC ............. 428/423.1, 480, 688, 446; 524/500, 524/537, 539
See application file for complete search history.

(56) References Cited

U.S. PATENT DOCUMENTS 5,914,193 A * 6/1999 Ono et al. ............ 428/451
6,617,393 B2 * 9/2003 Dworak et al. ............ 524/591
(Continued)

FOREIGN PATENT DOCUMENTS

| CN | 101037569 A | 9/2007 |
|---|---|---|
| JP | 06-082604 | 3/1994 |

(Continued)

OTHER PUBLICATIONS

English-Language Translation of the International Search Report for WO2012/036084.

*Primary Examiner* — Thao T. Tran
(74) *Attorney, Agent, or Firm* — Arthur M. Reginelli; Renner, Kenner

(57) ABSTRACT

A primer coating composition is provided for an optical article capable of forming a coating layer having excellent impact resistance, abrasion resistance, adhesion and high refractive index to an optical base material, having high refractive index, specifically a plastic lens without occurrence of poor appearance such as ununiformity, cloudiness, etc. and regardless of the materials of the plastic lens. A primer composition for an optical article may comprises urethane resin having a polycarbonate-derived skeleton, polyester resin, inorganic oxide fine particles and water, and water-soluble organic solvent, if necessary.

27 Claims, 3 Drawing Sheets

(51) Int. Cl.

| | | |
|---|---|---|
| G02B 5/23 | (2006.01) | |
| C09J 175/04 | (2006.01) | |
| C09J 167/02 | (2006.01) | |
| A61F 9/02 | (2006.01) | |
| C08G 18/44 | (2006.01) | |
| C08K 3/22 | (2006.01) | |
| C08L 67/00 | (2006.01) | |
| C08L 67/02 | (2006.01) | |
| C08L 69/00 | (2006.01) | |
| C08L 75/00 | (2006.01) | |
| C08L 75/04 | (2006.01) | |
| C08L 75/06 | (2006.01) | |
| C09D 5/00 | (2006.01) | |
| C09D 7/12 | (2006.01) | |
| C09D 167/02 | (2006.01) | |
| C09D 175/06 | (2006.01) | |
| G02B 1/10 | (2006.01) | |
| G03C 1/73 | (2006.01) | |
| G03C 1/93 | (2006.01) | |

(52) U.S. Cl.
CPC ................ *C08L 75/04* (2013.01); *C08L 75/06* (2013.01); *C09D 5/002* (2013.01); *C09D 7/1216* (2013.01); *C09D 167/02* (2013.01); *C09D 175/06* (2013.01); *G02B 1/04* (2013.01); *G02B 5/23* (2013.01); *G03C 1/733* (2013.01); *G03C 1/93* (2013.01)
USPC .......... 428/423.1; 428/480; 428/688; 428/446; 524/500; 524/537; 524/539

(56) References Cited

U.S. PATENT DOCUMENTS

| | | | |
|---|---|---|---|
| 7,410,691 B2 * | 8/2008 | Blackburn et al. ............ | 428/334 |
| 2009/0324956 A1 | 12/2009 | Otani | |

FOREIGN PATENT DOCUMENTS

| | | |
|---|---|---|
| JP | 2000-144048 | 5/2000 |
| JP | 2002-338883 | 11/2002 |
| JP | 2003-195003 | 7/2003 |
| JP | 2005-010618 | 1/2005 |
| JP | 2009-067845 | 4/2009 |
| JP | 2010-026183 | 2/2010 |
| JP | 2010-037394 | 2/2010 |
| JP | 2010-091995 | 4/2010 |
| WO | WO2004/078476 | 9/2004 |
| WO | WO2008/001875 | 1/2008 |
| WO | WO2010/119755 | 10/2010 |

* cited by examiner

PRIMER COMPOSITION FOR OPTICAL ARTICLES AND OPTICAL ARTICLES

TECHNICAL FIELD

This invention relates to a novel primer composition for an optical article comprising a urethane resin having a polycarbonate-derived skeleton and an inorganic oxide fine particle and to a novel optical article having a primer coating layer of high refractive index which is formed by curing said primer composition on an optical base material, specifically on the surface of a plastic lens. Further, this invention relates to a novel optical article (laminate) having a hard coating layer which is formed by curing a hard coating composition comprising inorganic oxide fine particles and an organosilicon compound on said primer coating layer on the surface of an optical base material. Further, this invention relates also to a novel optical article having a photochromic coating layer showing photochromic properties which is formed on said primer coating layer on the surface of an optical base material.

BACKGROUND ART

Since the surface of an optical base material, specifically that of a plastic lens is easy to be scratched as it is, because a synthetic resin constituting the plastic lens (a plastic lens material) is low in its abrasion resistance, a hard coating layer is usually formed on the surface of a lens. Usually, when laminating a hard coating layer, its abrasion resistance can be improved; it has been known that the impact resistance of the plastic lens is decreased. Further, in order to inhibit reflected light from the plastic lens, an antireflection coating layer is laminated on the hard coating layer by depositing an inorganic oxide on the hard coating layer. It has been, however, known that when the antireflection coating layer is laminated on the hard coating layer previously laminated on the surface of the plastic lens, the impact resistance of the plastic lens is lowered more increasingly to be easily cracked. It has been, therefore, studied that a primer coating layer is inserted between a plastic lens and a hard coating layer for the purpose of improving the impact resistance. For a plastic lens of high refractive index, the refractive index of a primer coating layer laminated is important. This is because that an interference pattern is generated caused by the difference in refractive index between the plastic lens and the primer coating layer.

As a primer composition for a plastic lens of high refractive index that using a urethane resin has been usually known. Specifically, (i) a primer composition comprising a mixture of a urethane resin and inorganic oxide fine particles (Patent Literature 1), (ii) that comprising a mixture of a urethane resin, inorganic oxide fine particles and a hydrate of an organosilicon compound (Patent Literature 2), (iii) that comprising a mixture of a urethane resin, inorganic oxide fine particles and a urethane-forming monomer- and/or oligomer (Patent Literature 3), etc. have been known. Further, (iv)) a primer composition using a polyester resin and inorganic oxide fine particles has been also known (Patent Literature 4).

Such primer compositions as described above can give good adhesion to a specific plastic material and can improve the impact resistance of the specific plastic material. However, these primer compositions have problems that the adhesion is insufficient depending on the types of plastic materials constituting a plastic lens. In a case of a primer composition comprising a mixture of a urethane resin and inorganic oxide fine particles, there is a case where a primer coating layer formed is whitened, and there has been, therefore, still room for improvement.

Specifically, a primer composition disclosed in Patent Literature 1 has problems that it requires long time for curing of a primer coating layer and is inferior in workability, productivity, etc., in addition to such problems as described above. It has been considered that the causes of those problems are characteristics of a urethane resin itself used and an organic solvent added to a primer composition.

A primer composition disclosed in Patent Literature 2 has problems that the adhesion is insufficient depending on the types of plastic lens materials and a primer coating layer formed is whitened (due to the use of inorganic oxide fine particles as a mixture with a urethane resin). In addition to that, a primer composition disclosed in Patent Literature 2 has a problem in the storage stability sustainable to long term use due to the use of a hydrate of an organosilicon compound.

A primer composition described in Patent Literature 3 comprises an urethane-forming monomer as a third constituent component in addition to a urethane resin and inorganic fine particles. It is necessary to cure the urethane-forming monomer in order to form a primer coating layer. A curing treatment is carried out for a primer coating layer at high temperatures after coating the surface of a plastic lens with the primer composition. Therefore, when using such a primer composition for a plastic lens of low heat resistance, there are problems that a plastic lens is thermal-deformed or colored etc. Further, there has been a problem that the storage stability of a primer composition is not sufficient because of the use of a reactive urethane-forming monomer.

Patent Literature 4 describes a primer composition comprising a polyester resin and describes that inorganic oxide fine particles can be added to the primer composition. As a result of the study of the inventors of this invention, however, it has become clear that a primer composition comprising a polyester resin and inorganic oxide fine particles has a problem that the adhesion is insufficient depending on the types of plastic lens materials.

In recent years, an aqueous dispersion of urethane resin has been used for a primer composition for improving the impact resistance of plastic lens from the view point of environmental problems. However, when an aqueous dispersion of urethane resin is used, there are many problems in low wettability to a plastic lens and appearance of the coating such as smoothness, etc. In order to solve such problems, an organic solvent is added for improvement of the wettability and the smoothness of the coating. However, a new problem occurs sometimes in that the storage stability of the primer composition itself lowers.

For an optical article such as a plastic lens, etc., a photochromic coating layer comprising a photochromic compound is formed on the surface of a plastic lens in order to give a photochromic properties to a plastic lens. The photochromic properties herein used are defined as a reversible action in which when an object is irradiated with light comprising ultraviolet rays such as sunlight, light of a mercury vapor lamp, etc., it becomes discolored rapidly, and when irradiation of light is terminated and it is placed in a dark place, it returns to its original color. Such a photochromic coating layer is formed by applying a photochromic coating agent comprising a photochromic compound and a polymerizable monomer on the surface of a plastic lens and then curing it (hereinafter such a method of forming a photochromic coating layer is referred to as just "coating method" as the case may be).

In the coating method of a prior art, a photochromic coating layer is formed directly on the plastic lens. In recent years, however, in order to improve more highly the adhesion of the photochromic coating layer and the plastic lens, a method has been adopted for forming a photochromic coating layer after forming a primer coating layer on a plastic lens. Specifically, in order to form the primer coating layer for the photochromic coating layer, a method has been known of using a primer composition comprising a moisture-curable polyurethane resin (Patent Literature 5) or a primer composition comprising urethane resin emulsion (Patent Literature 6). These methods can enhance the adhesion of the photochromic coating layer and the plastic lens. There is, however, still room for improvement in the respects described below:

That is to say, in the method described in Patent Literature 5, a primer composition comprising a moisture-curable polyurethane resin and/or its precursor, and a solvent having a boiling point of 70° C. and above and a solubility parameter of eight (8) and above is used. However, when a primer coating layer is formed on the surface of a plastic lens of a polycarbonate, it occurs that a solvent constituting the primer composition dissolves excessively the surface of the plastic lens. In order to prevent that, a different film or layer for prevention must be newly formed on the surface of the plastic lens. Therefore, there is still room for improvement in operability. Such a primer composition comprises inorganic oxide fine particles. There is, however, a problem that a refractive index is low, because of difficulty of mixing of inorganic oxide fine particles.

In the method described in Patent Literature 6, a primer composition comprising an emulsion in which a urethane resin is colloidal dispersed in a dispersion medium. By the use of such a primer composition, the adhesion of plastic lens and a photochromic coating layer can be sufficiently secured. There is, however, a problem that when inorganic oxide fine particles are mixed, the primer coating layer is whitened.

As described above, in the primer composition used in the production of a photochromic plastic lens according to the coating method, the development of a primer composition applicable to a plastic lens of various types of materials has been expected. Further, the development of a primer composition has been expected which is capable of improving not only the impact resistance of a plastic lens, but also the adhesion of a plastic lens and a photochromic coating layer.

CITATION LIST

Patent Literature

PTL 1: Japanese Patent Publication (Toku-kai) 2002-338883
PTL 2: Japanese Patent No. 2896546
PTL 3: Japanese Patent Publication (Toku-kai) 2009-67845
PTL 4: Japanese Patent No. 3362306
PTL 5: International Publication WO 04/078476, pamphlet
PTL 6: International Publication WO 08/001,875, pamphlet

SUMMARY OF INVENTION

Problems to be Solved by Invention

Accordingly, a general object of this invention is to provide a primer composition for an optical article having excellent storage stability itself which not only improves the impact resistance of an optical base material (a plastic lens), but also forms a film (coating layer) which has uniform smoothness, does not bring about fault in appearance such as cloudy-whitening, etc. and is excellent in the adhesion with the optical base material.

A specific object of this invention is to provide a primer composition for an optical article which exhibits excellent abrasion resistance, impact resistance and which is able to reduce an interference pattern between the optical article and a primer coating layer when the primer coating layer obtained by the primer composition is formed on the optical base material and then a hard coating layer formed by inorganic oxide fine particles and a hydrolyzable group-containing organosilicon compound is laminated thereon.

Still, a further specific object of this invention is to provide a primer composition for an optical article which can improve also the adhesion of a photochromic coating layer and an optical base material when a primer coating layer obtained by the primer composition is formed on the optical base material and then the photochromic coating layer is formed on the primer coating layer.

Means for Solving the Problems

We have studied devotedly in order to solve the above-described problems. As a result, we have found it is necessary to use urethane resin having a specific structure (physical properties) in order that the appearance of an optical article obtained is improved more highly, and that performances such as the impact resistance, abrasion resistance, adhesion, etc. are superior to those of a prior art, and that the storage stability of the primer composition itself is also improved, and accomplished this invention.

Further, we have found that such a primer composition comprising the constituent component as described above can improve also the adhesion of an optical base material and a photochromic coating layer comprising a photochromic compound and accomplished this invention.

A first object of this invention is to provide a primer composition for an optical article comprising;
(A) a urethane resin having a polycarbonate-derived skeleton (hereinafter referred to as just [A-component]);
(B) a polyester resin (hereinafter referred to as just [B-component]);
(C) inorganic oxide fine particles (hereinafter referred to as just [C-component]);
(D) water (hereinafter referred to as just [D-component]);
wherein the weight ratio of B-component is from 10 to 95 weight parts, C-component is from 70 to 30 weight parts and D-component is from 150 to 2300 weight parts to 100 parts by weigh of A-component.

For the above-described a primer composition for an optical article, an A-component is preferably a urethane resin having a polycarbonate-derived skeleton and the elongation of 200 to 1000%.

A second object of this invention is to provide an optical article having on an optical base material a primer coating layer obtained by curing the above-described primer composition for an optical article.

An excellent effect can be exhibited for the above-mentioned optical article of the second object in cases where the above-described optical base material is a photochromic optical base material, particularly where the photochromic optical base material has a photochromic coating layer obtained by curing a photochromic curing composition comprising a photochromic compound.

A third object of this invention is to provide a laminate having a hard coating layer obtained by curing a hard coating composition comprising inorganic oxide fine particles and a hydrolyzable group-containing organosilicon compound on the primer coating layer of the optical article of the afore-mentioned second object.

A fourth object of this invention is to provide a first laminated article having a photochromic coating layer obtained by curing a photochromic curing composition comprising a photochromic compound on the primer coating layer of an optical article, formed by the primer composition for the optical article of the afore-mentioned first object.

A fifth object of this invention is to provide a second laminated article having a primer coating layer formed by the primer composition for the optical article of the above-described first object on the photochromic coating layer of the first laminated article of the above-described fourth object.

A sixth object of this invention is to provide a third laminated article having a hard coating layer obtained by curing a hard coating composition comprising inorganic oxide fine particles and a hydrolyzable group-containing organosilicon compound on the primer coating layer of the second laminated article of the above-described fifth object.

Advantageous Effects of Invention

The primer composition for an optical article of this invention can improve the adhesion between an optical base material, specifically, a plastic lens and a hard coating layer and can improve the impact resistance of an optical base material (an optical article) having such a hard coating layer. Further, a plastic lens having a reflection-prevention coating layer laminated on the hard coating layer has sufficient impact resistance and high resistance against cracking and is sufficiently practically used. Furthermore, the primer composition for the optical article of this invention has high refractive index. Therefore, when it is applied to a lens of high refractive index, an interference pattern caused by the difference in the refractive index between the optical article and the primer coating layer formed can be reduced. In addition to that, cloudy-whitening in the primer coating layer is little, and the primer coating layer having excellent appearance can be formed. The primer coating composition for an optical article of this invention has excellent storage stability.

An optical article having a primer coating layer obtained by curing the primer composition for an optical article of this invention has excellent impact resistance compared with a plastic lens on which only a hard coating layer is laminated and its adhesion of the hard coating layer is high. Further, by the use of the primer composition for an optical article of this invention, an optical base material provided with a hard coating layer of high quality having high refractive index, excellent abrasion resistance and appearance can be obtained.

The primer composition for an optical article of this invention can exhibit excellent advantageous effect in case where an optical base material is a photochromic optical base material. The primer composition for an optical article of this invention can exhibit special excellent effect, specifically in a case where the photochromic optical base material is an optical base material on which a photochromic coating layer is formed. In that case, at least a primer coating layer formed of the primer composition for an optical article of this invention is formed on the photochromic coating layer.

Further, the primer composition for an optical article of this invention can improve the adhesion of an optical base material and a photochromic coating layer. When the primer composition for an optical article of this invention is used for such applications, a primer coating layer made of the primer composition for an optical article of this invention is formed on the plastic base material, and then the photochromic coating layer is formed on the primer coating layer.

As described above, the primer composition for an optical article of this invention can improve the adhesion of an optical base material and a hard coating layer, the adhesion of the optical base material and a photochromic coating layer, and the adhesion of the photochromic coating layer and the hard coating layer. Further, the primer composition for an optical article of this invention can improve the impact resistance of the optical article having such coating layers.

DESCRIPTION OF EMBODIMENTS

Figure 1:
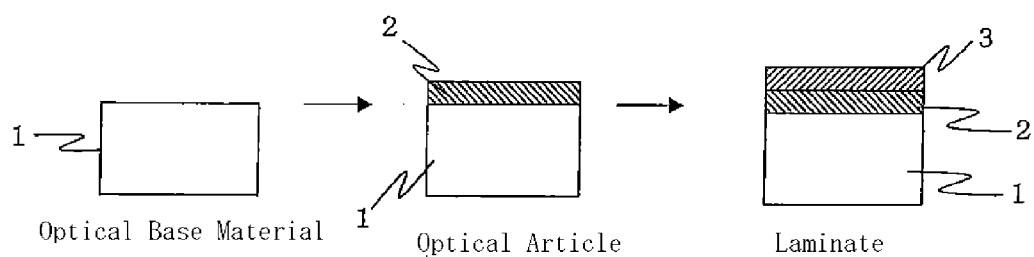
FIG. 1 is a flow diagram of a working embodiment for production of a laminate of this invention.

This invention is detailed below:
The primer composition for an optical article of this invention is characterized by comprising;
(A) a urethane resin having a polycarbonate-derived skeleton (hereinafter referred to as just [A-component]);
(B) a polyester resin (hereinafter referred to as just [B-component]);
(C) inorganic oxide fine particles (hereinafter referred to as just [C-component]); and
(D) water (hereinafter referred to as just [D-component]);
wherein the weight ratio of B-component is from 10 to 95 weight parts, C-component is from 70 to 30 weight parts and D-component is from 150 to 2300 weight parts to 100 parts by weigh of A-component.

"A primer composition for an optical article" is applied to an optical base material, specifically a plastic lens and improves the impact resistance of the optical article obtained. A primer coating layer made of the primer composition for an optical article is formed between the optical base material and a hard coating layer or photochromic coating layer which are detailed below and can improve the adhesion of the hard coating layer or photochromic coating layer to the optical base material. Specifically, the primer composition for an optical article can improve the impact resistance of the optical base material having the hard coating layer.

Each of the components of the primer composition for an optical article of this invention is described:

A Urethane Resin Having a Polycarbonate-Derived Skeleton (A-Component)

The primer composition for an optical article of this invention comprises a urethane resin having a polycarbonate-derived skeleton (A-component). The shape (form) and properties of the urethane resin used in this invention are not specifically limited, so long as it is capable of being dispersed in water and solvent to form a primer composition. Above all, it is preferable to use an aqueous dispersion of the urethane resin, that is, an aqueous dispersion in which the urethane resin is previously dispersed in water, taking the easiness of preparation of the primer composition, easiness of availability of the urethane resin into consideration.

Since the urethane resin of A-component has a polycarbonate-derived skeleton, it comprises a reaction product of polycarbonate polyol and polyisocyanate. Generally, polyalkylene glycol, polyester polyol, polyether polyol, polyether.ester polyol, etc. may be used as polyol constituting the urethane resin. However, taking the adhesion and impact resistance with various types of plastic lens materials constituting an optical base material, specifically a plastic lens into consideration, it is important to use polycarbonate polyol. That is to say, this invention is capable of exhibiting excellent advantageous effect.

As the polycarbonate polyol, known polycarbonate polyol may be used without limitations, and poly(alkylene carbonate) such as poly(hexamethylene carbonate), etc. may be exemplified.

Illustrative examples of the afore-mentioned polyisocyanate include an aromatic isocyanate compound such as tolylenediisocyanate, 4,4-diphenylmethanediisocyanate, xylenediisocyanate, 1,5-naphthalenediisocyanate, toluidinediisocyanate, phenylenediisocyanate, 4,4-diphenyldiisocyanate, dianisidinediisocyanate, 4,4-diphenyletherdiisocyanate, triphenylmethanetriisocyanate, tris(isocyanatephenyl)thiophosphate, tetramethylxylenediisocyanate, etc.; and an aliphatic isocyanate compound such as 1,3,3-trimethylhexamethylenediisocyanate, 4,4'-, 2,4'-, or 2,2'-dicyclohexylmethanediisocyanate or mixture thereof, hexamethylenediisocyanate, isophoronediisocyanate, hydrogenated xylenediisocyanate, lysinediisocyanate, lysineestertriisocyanate, 1,6,11-undecanetriisocyanate, 1,8-diisocyanate-4-isocyanatemethyloctane, 1,3,6-hexamethylenetriisocyanate, bicycloheptanetriisocyanate, etc.

The urethane resin used in this invention is composed of the afore-mentioned polycarbonate polyol and the afore-mentioned polyisocyanurate, but may contain polyisocyanate having one or more sulfur or halogen atoms, and denaturants such as biuret, isocyanurate, allophanate, carbodiimide, etc.

Further, as the urethane resin used in this invention, it is preferable to use the urethane resin having a crosslinking structure. By the use of the urethane resin having a crosslinking structure in a molecule, when a coating composition for forming a hard coating layer is applied to a primer coating layer, it is possible to enhance the dissolution resistance of the primer coating layer against the coating composition to shorten the production time for a laminate. And, a laminate thus obtained is excellent in appearance and impact resistance.

The elongation of a urethane resin of A-component of the coating composition of this invention may be preferably 200~1000%. When the elongation meets the afore-mentioned range, the properties of an optical article obtained are improved, specifically its impact resistance can be improved; it is considered that the reason for this may be possibly that the primer coating layer obtained has moderate flexibility. Further, When the elongation meets the afore-mentioned range, the abrasion resistance of the hard coating layer is improved and simultaneously the impact resistance of the laminate obtained (an optical base material having a hard coating layer) is improved, specifically when a hard coating layer is formed by curing a hard coating composition comprising inorganic oxide fine particles and an organosilicon compound on the primer coating layer; the reason for this may be possibly that the primer coating layer does not become soft excessively. Since the elongation of the urethane resin meets the above-described range in the use of the improvement of the adhesion of a photochromic coating layer and an optical base material (the uses for production of a first, second and third laminated articles), the adhesion can be improved sufficiently.

Accordingly, taking the performances of the optical article, laminate, the first laminated article obtained into consideration, the elongation of urethane resin is preferably from 200 to 1000%, more preferably from 250 to 900%, The elongation of urethane resin is a value measured in such a manner as described below. The method of the measurement for a case when using an aqueous dispersion of a urethane resin is described below: Firstly, an aqueous dispersion comprising a urethane resin is put into a container such as a chalet so that the film thickness of the urethane resin after drying becomes about 500 μm, dried at a room temperature for 24 hours, dried at a temperature of 80° C. for 6 hours, and then dried at a temperature of 120° C. for 20 minutes to prepare a film of urethane resin. Thereafter, the film of urethane resin is cut off in size 15 mm (width)×200 mm (length), and then a test piece is prepared in the mid section of which marks are produced at equal intervals of 50 mm. Such a test piece thus prepared is attached to a tensile testing machine, and then the elongation is measured by pulling the test piece at a speed of 200 mm/minutes with a distance between grips of 100 mm to be fractured. The measuring temperature is 23° C. The elongation of a urethane resin contained in a primer composition can be measured in such a manner as described above by preparing a film of a urethane resin. The elongation is calculated in such a manner as described below:

Elongation (%)=((distance between marks at the time of fracture−distance between marks before the test)/(distance between marks before the test))×100

It is preferable that the urethane resin has the elongation of 200~1000% measured in such a manner as described above and simultaneously 100% modulus of 1.5 to 18N/mm$^2$. The 100% modulus is a value measured simultaneously with the above-described elongation and means the stress when the length of the afore-mentioned film of urethane resin (test piece) is 2 (two) times (elongation of 100%) the length before the test (distance between grips before the test). Since the 100% modulus of urethane resin satisfies the above-described range, the performances of an optical article, laminate, first laminated article, etc. obtained can be improved.

While the urethane resin of A-component used in this invention is not specifically limited, its glass transition point (Tg) is preferably less than 0° C., more preferably −5° C. and below and most preferably −10° C. and below. By the use of the urethane resin having Tg of less than 0° C., the impact resistance and adhesion of an optical article, laminate, first laminated article, etc. can be more improved. While the lowest limit of Tg of the urethane resin is not particularly limited, it is preferably −100° C. and above, more preferably −70° C. and above, and most preferably −50° C. and above, taking the productivity of urethane resin and performances of an optical article, laminate, first laminated article, etc. obtained into consideration.

The glass transition point (Tg) of the urethane resin is a value measured in such a manner as described below: The similar test piece to the film of urethane resin used for measurement of its elongation was used as a test piece for measurement of Tg. By the use of such a test piece, Tg was measured by means of "DMS 5600" (trade name for a dynamic viscoelasticity measuring device manufactured by SIT Co., Ltd.). The measurement was carried out under conditions, that is, deformation mode; tension, speed of rise of temperature; 5° C./minutes, measuring frequency; 10 Hz, range of measuring temperature; −100° C. to 200° C. The glass transition point (Tg) of the urethane resin contained in the primer composition can be measured in such a manner as described above by preparation of a film of the urethane resin.

As described above, it is preferable in this invention to use previously-prepared aqueous dispersion of urethane resin as a urethane resin, taking the easiness of the production of the primer composition into consideration. When using such an aqueous dispersion, it is preferable that the average particle diameter of the urethane resin in the aqueous dispersion is more than 50 nm and 140 nm or below. When the average particle diameter is more than 140 nm, it is possible to remove a urethane resin having a relatively large diameter by filtration to make its average diameter 140 nm or below for usable. While the method of the filtration is not specifically limited, it is possible to make its average diameter 140 nm or below by the use of a filter, for example, a TCG-type filter (glass-filter-paper cartridge-type filter, a type name of a filter manufactured by ADVANTEC MFG. INC.) When the average particle diameter is more than 140 nm, the storage stability of the primer composition itself tends to lower, when lower alcohol is added for the purpose of the improvement of wettability to an optical base material. It is possibly considered that the reason is that since a urethane resin is easy to swell in lower alcohol, viscosity increases as the amount of addition of lower alcohol increases. On the other hand, when the average particle diameter of the urethane resin in the aqueous dispersion is 50 nm or below, it is hard to prepare an aqueous dispersion of the urethane resin itself. Since the average particle diameter of the urethane resin in the aqueous dispersion satisfies the above-described range, an uniform film (primer coating layer) having excellent smoothness can be formed and consequently an optical article having excellent appearance can be obtained, when it is combined with an organic solvent as detailed below. The average particle diameter of a urethane resin in the aqueous dispersion is a value measured by a laser diffraction scattering particle size distribution measuring device "LS230" (trade name for Beckman Coulter Co. Ltd.). The particle diameter of the urethane resin was measured by means of an optical diffraction method using laser having wavelength of 750 nm and such a measuring device. The average particle diameter in this invention is a volume average value measured by such a method.

The concentration of the urethane resin in an aqueous dispersion (the concentration of the solid content of the urethane resin) may be determined properly depending on the different types of requirements, for example objective for use, etc. and may be preferably from 20 to 60 wt %. By the use of the aqueous dispersion of the urethane resin satisfying such range of the concentration, handling is easy and the concentration of the urethane resin of the primer composition obtained may be easily controlled.

As the aqueous dispersion of urethane resin which satisfies the above-described requirements, commercially available ones may be used; specifically "SUPERFLEX" series (manufactured by Dai-ichi Kogyou Seiyaku Co. Ltd. and registered trade mark), "NEOSTECKER" series and "EVAFANOL" series (manufactured by NICA CHEMICAL Co., Ltd. and both are registered trade mark), "HYDRAN" series (manufactured by DIC Corporation and registered trade mark) are exemplified.

Polyester Resin (B-Component)

The primer composition for an optical article of this invention comprises a polyester resin as a B-component. The shape (form) and properties of the polyester resin used in this invention are not specifically limited, so long as it is capable of being dispersed in water and solvent to form a primer composition. Above all, it is preferable to use an aqueous dispersion of urethane resin, that is, an aqueous dispersion in which the urethane resin is previously dispersed in water, taking the easiness of preparation of the primer composition, easiness of availability of the urethane resin into consideration.

The polyester resin as a B-component is a resin prepared by polycondensation of polybasic acid and polyhydric alcohol and contains no urethane bond (—NHCOO—) in its molecule.

Among the polyester resins, it is preferable to use polyester elastomer the glass transition point (Tg) of which satisfies the range described below. Preferably, the polyester elastomer is composed of a copolymer comprising a hard segment and a soft segment. Specifically, a polyester.polyether-type-polyester elastomer comprising a polyester as a hard segment and a polyether as a soft segment and a polyester.polyester elastomer comprising a polyester as a hard segment and a polyester as a soft segment may be preferably used. The weight ratio of the hard segment and the soft segment may be preferably the range of 30/70~90/10, more preferably the range of 40/60~80/20. By the use of the polyester resin the weight ratio of the hard segment and the soft segment of which satisfies the above-described range, a primer coating layer having sufficient mechanical strength, heat-resistance and impact-resistance can be formed.

As the hard segment constituent component of the above-described polyester elastomer may be preferably used polyester comprising dicarboxylic acid as polybasic acid and low-molecular weight glycol as polyhydric alcohol.

As the above-described dicarboxylic acid constituting the polyester of the hard segment may be exemplified by aromatic dicarboxylic acid such as terephthalic acid, isophthalic acid, phthalic acid, 2,6-Naphthalene dicarboxylic acid, etc.; straight-chain saturated aliphatic dicarboxylic acid having 4~20 carbon atoms such as succinic acid, adipic acid, azelaic acid, decamethylene dicarboxylic acid, octadecane dicarboxylic acid, etc.; aliphatic hydroxycarboxylic acid such as $\epsilon$-oxycaproic acid, etc.; dimer acid (dibasic acid formed by dimerization-polymerization of aliphatic monocarboxylic acid having a double bond), etc., and ester-forming derivatives thereof.

On the other hand, as low-molecular weight glycol, aliphatic glycol such as ethylene glycol, trimethylene glycol, 1,4-butanediol, 1,5-pentanediol, 1,6-hexanediol, neopentyl glycol, etc.; alicyclic glycol such as 1,6-cyclohexanedimethanol, etc. and ester-forming derivatives thereof may be exemplified.

As the soft segment of the polyester elastomer, the aforementioned polyester or polyether may be preferably used.

The polyester constituting the soft segment may be exemplified by that comprising dicarboxylic acids and long-chain glycol (polyhydric alcohol). For the dicarboxylic acid forming the polyester of the soft segment the same dicarboxylic acid as that forming the polyester of the afore-mentioned hard segment may be used. On the other hand, as the long-chain glycol poly(1,2-butadiene glycol), poly(1,4-butadiene glycol) and a hydrogenated product thereof, etc. may be exemplified. Further, $\epsilon$-caprolacton and enantholactone may be also used as the polyester component.

As the polyether constituting the soft segment, poly(alkylene oxide)glycol such as poly(ethylene oxide)glycol, poly(1,2-propylene oxide)glycol, poly(1,3-propylene oxide)glycol, poly(tetramethylene oxide)glycol, etc. may be exemplified.

A polyester elastomer (polyester resin) suitably used in this invention comprises preferably copolymer of the above-described hard segment and soft segment; above all, a polyester elastomer (polyester resin) the glass transition point (Tg) of which satisfies such range as described below. That is to say, its glass transition point (Tg) is preferably less than 0° C., more preferably −5° C. and below and most preferably −10° C. and below. By the use of the polyester resin having Tg of less than 0° C., the impact resistance and adhesion of an optical article, laminate, first laminated article, etc. can be more improved. While the lowest limit of Tg of the polyester resin is not particularly limited, it is preferably −100° C. and above, more preferably −70° C. and above, and most preferably −50° C. and above, taking the productivity of polyester resin and performances of the optical article, laminate, first laminated article, etc. obtained into consideration.

The glass transition point (Tg) of the polyester resin is a value measured the same manner as described for the above-described A-component.

The number average molecular weight of the polyester resin suitably used in this invention is preferably the range of 500~100000, more preferably the range of 6000~50000.

The molecular weight of the above-described polyester resin was measured by the use of a gel permeation chromatography (GPC) with polystyrene conversion under such conditions as described below:

Column: Shodex KD-805, KD-804 (manufactured by Showa Denko K.K.)
Eluent: tetrahydrofuran solution
Flow rate: 1 ml/min.
Detector: RI detector
Polyester resin sample solution: 0.5 weight % tetrahydrofuran solution.

As afore mentioned, it is preferable to use a polyester resin in the state of an aqueous dispersion. In that case, the concentration of the polyester resin in the aqueous dispersion (the concentration of the solid content of the polyester resin) may be determined properly depending on the different types of requirements, for example objective for use, etc. and may be preferably from 10 to 50 wt %. By the use of the aqueous dispersion of the polyester resin satisfying such range of the concentration, the concentration of the polyester resin obtained is easily controlled. The aqueous dispersion may contain such a water-soluble organic solvent as detailed below in the amount of ⅓ or below of water used.

As the aqueous dispersion of the polyester resin that satisfies the above-described requirements, commercially available one may be used. Specifically, "PESRESIN" series (manufactured by TAKAMATSU OIL FAT CO., LTD. and trade name), "VYLONAL" series (manufactured by TOYOBO CO., LTD. and trade name), "ARON MELT" series (manufactured by Toagosei Company, Limited. and registered trade mark, etc. are exemplified.

Inorganic Oxide Fine Particles C-Component)

In the primer composition for an optical article of this invention, inorganic oxide fine particles (C-component) are used. By adding C-component, the refractive index of the primer coating layer formed can be improved to decrease an interference band generated by the difference in the refractive index between the primer coating layer and an optical base material, and the abrasion resistance of the hard coating layer can be more improved Since C-component is added in order to enhance the refractive index, the inorganic oxide fine particles used may be preferably fine particles of an inorganic oxide or complex inorganic oxide comprising at least one element selected from the group consisting of Ti, Zr, Sn, Sb and Ce. For the complex inorganic oxide, it may contain Si, Al, Fe, In, Au, W, etc. other than the afore-mentioned elements.

The particle diameter of C-component may be preferably primary particle diameter of around 1~300 nm observed by a transmission electron microscope (TEM).

The inorganic oxide fine particles having such particle diameter are usually used as a sol formed by dispersing in water or water-soluble organic solvent (specifically alcohol family solvent) as a dispersing medium; colloidal dispersion is generally used to prevent fine particles from being coagulating. For example, in this invention the inorganic oxide fine particles are added in the form of a sol in which they are dispersed in water soluble organic solvent or water in the primer composition for an optical article, from the view point that they are dispersed homogeneously in the primer composition for an optical article.

For the water soluble organic solvent used for a dispersing medium for C-component, an alcohol solvent such as isopropanol, ethanol, methanol, ethylene glycol, etc. may be preferable; however methylethylketone, methylisobutylketone, dimethylacetamide, etc. may be used.

In this invention, it is preferable that C-component is mixed with other components in the form of a sol in which C-component is dispersed in water or water-soluble organic solvent, specifically in the form of aqueous sol or water-soluble organic solvent sol of inorganic oxide fine particles or complex inorganic oxide fine particles.

The pH of sol solution in which inorganic oxide fine particles are dispersed may be preferably the range of 5.0~10.0, more preferably the range of 5.5~9.0 form the view point that they are dispersed homogeneously in the primer composition for an optical article. The value of the pH is that obtained by diluting a sample solution ten (10) times with distilled water and measuring by a pH meter "D-51" (manufactured by HORIBA, Ltd.).

Sol of the complex inorganic oxide fine particles may be also commercially available; for example, "HX series" "HIT series" "HT series" "HZ series" "AMT series", etc. manufactured by NISSAN CHEMICAL INDUSTRIES, LTD. are exemplified. Among them, HX series" "HT series" and "HZ series" may be preferable, taking high refractive index and dispersion-stability into A-component and B-component into consideration.

Water (D-Component)

The primer composition for an optical article of this invention comprises water (D-component).

The water for D-component includes water contained in an aqueous dispersion of urethane resin as A-component in the preparation of the primer composition, water contained in an aqueous dispersion of polyester resin as B-component in the preparation of the primer composition, water used as dispersing medium in an aqueous dispersion of urethane resin, or water used as dispersing medium in an aqueous dispersion of polyester resin. When using the aqueous sol of inorganic oxide fine particles as C-component, the water for D-component includes also water used as a dispersing medium of the aqueous sol, By the use of water, the storage stability of the primer composition is improved and working surroundings are also improved.

Since when the primer composition is used for the formation of a primer coating layer by a dip-coating method, the primer composition has to be for a long time in a dip-coating cell, these advantageous effects are particularly useful.

Water-Soluble Organic Solvent (E-Component)

The primer composition for an optical article may comprise a water-soluble organic solvent (E-component). The water-soluble organic solvent improves the wettability of the primer composition. Further, when dispersing sol of the water-soluble organic solvent of the inorganic oxide fine particles is used as the afore-mentioned C-component, its dispersing medium is used as water-soluble organic solvent. The water-soluble organic solvent is defined as an organic solvent having the solubility in water at a temperature of 25° C. of 5 weight % or above.

As the E-component, alcohols such as methanol, ethanol, isopropyl alcohol, n-butanol, t-butanol, etc.; organic solvents having 2~7 carbon atoms and hydroxyl groups of 2 or above in a molecule such as ethylene glycol, propylene glycol, diethylene glycol, dipropylene glycol, cyclohexanediol, trimethylene glycol, tripropylene glycol, 1,2-butanediol, 1,3-butanediol, 1,4-butanediol, 1,4-butendiol, hexylene glycol, trimethylolpropane, pentaerythritol, 1,5-pentanediol glycerin, glycerin monoacetate, etc.; ethers such as ethylene glycol monomethyl ether, ethylene glycol monoisopropyl ether, ethylene glycol monoethyl ether, ethylene glycol mono-n-propyl ether, ethylene glycol mono-n-butyl ether, ethylene glycol mono-t-butyl ether, propylene glycol monomethyl ether, propylene glycol monoethyl ether, propylene glycol mono-n-propyl ether, propylene glycol mono-n-butyl ether, propylene glycol monomethyl ether, acetate, propylene glycol monoethyl ether acetate, dioxane, etc.; and ketones such as diacetone alcohol, etc. are exemplified. Specifically, organic solvents having 3~9 carbon atoms and an ether bond or carbonyl bond in a molecule and one hydroxyl group in a molecule such as diacetone alcohol, ethylene glycol monoisopropyl ether, ethylene glycol monoethyl ether, ethylene glycol mono-n-butyl ether, ethylene glycol mono-t-butyl ether, propylene glycol monomethyl ether, propylene glycol monoethyl ether, diethylene glycol monobutyl ether, dipropylene glycol-n-propyl ether, etc.; and aprotic polar solvent such as N-methylpyrrolidone, N,N-dimethylformamide, dimethyl sulfoxide, etc. are exemplified. Specifically, in order to enhance the wettability of the primer composition to an optical base material and to exhibit the effect of suppression of repellency and to maintain the storage stability of the primer composition, it is preferable to use methanol, ethylene glycol, propylene glycol, diacetone alcohol, propylene glycol mono-n-butyl ether, ethylene glycol mono-butyl ether, diethylene glycol mono-butyl ether or dipropylene glycol-n-propyl ether; these may be used independently or as a mixture of two or more kinds. Taking the wettability of the primer composition to a plastic lens and transparency into consideration, it is preferable to comprises propylene glycol mono-n-butyl ether. This E-component is used independently or as a mixture of two or more kinds.

Blending Amount of Each of the Components

Blending Ratio of Each of A-Component and B-Component and C-Component

The primer composition for an optical article of this invention comprises (A) urethane resin, (B) polyester resin, and (C) inorganic oxide fine particles.

Taking the refractive index and appearance of the primer coating layer formed, the impact resistance of an optical article, the adhesion of the optical base material and a hard coating layer or a photochromic coating layer, etc. into consideration, the blending amount of these components should be those described below:

That is to say; to 100 parts by weight of A-component (when using aqueous dispersion, solid content obtained by concentrating and drying the aqueous dispersion of urethane resin: weight of urethane resin), B-component (when using aqueous dispersion, solid content obtained by concentrating and drying the aqueous dispersion of polyester resin: weight of polyurethane resin) is 10~95 parts by weight and C-component (hereinafter, when showing the blending ratio of each of components to this Resin, it is sometimes described as blending ratio to urethane resin) is 70~300 parts by weight.

When B-component is less than 10 parts by weight, the dispersion-stability of inorganic oxide fine particles (C-component) to urethane resin (A-component) as a main component of a primer coating layer is not sufficient and a laminate etc. obtained is whitened; so, it is not preferable. On the other hand, when B-component is 95 parts by weight or above, the adhesion to an optical base material lowers; so, it is not preferable.

When C-component is less than 70 parts by weight, the primer composition obtained has not sufficient high refractive index and the impact resistance after lamination of a hard coating layer lowers; so it is not preferable. On the other hand, when C-component is 300 parts by weight or above, the primer coating layer obtained is whitened, the adhesion to an optical base material lowers, the impact resistance of an optical article lowers, etc.; so it is not preferable.

Taking the dispersion-stability of the inorganic oxide fine particles, the adhesion to an optical base material, the impact resistance of an optical article into consideration, to 100 parts by weight of urethane resin, B-component is preferably 20~90 parts by weight, more preferably 30~85 parts by weight. C-component is preferably 80~205 parts by weight, more preferably 100~200 parts by weight to 100 parts by weight of urethane resin.

(D) Blending Amount of Water

According to the present invention, water (D-component) is used in 150~2300 parts by weight to urethane resin (A-component). When water used is 150 parts by weight or below, the storage stability is not sufficient. So it is not preferable. When water used is 2300 parts by weight or above, a flat primer coating layer is hard to be formed. So it is not preferable. By adding water in the above-described range, the primer composition for an optical article of this invention can enhance the storage stability in higher. When the primer coating layer is formed by applying the primer composition by means of a dip-coating method, coating, the primer composition has to be stored in a dip-coating cell for a long periods. It is, therefore, specifically useful to use water in the above-described range.

It is, further, preferable to adjust the blending amount of water used in the above-described corresponding the uses of the primer composition for an optical article of this invention.

Specifically, for the primer coating composition for an optical article of this invention used to laminate a hard coating layer, the blending amount of water is 150~2300 parts by weight to 100 parts by weight of urethane resin. In that case, by making the blending amount of water satisfy the above-described range, the storage stability is enhanced in higher and the wettability of the primer coating layer with the hard coating layer is improved, and therefore repellency is absent and further the occurrence of the poor appearance such as running, etc. may be suppressed. More preferably, the blending amount of water is 300~2000 parts by weight to 100 parts by weight of urethane resin; more preferably, it is 500~1900 parts by weight.

On the other hand, when the primer composition is used for the formation of a primer coating layer for lamination of a photochromic layer (when using a first laminate), the blending amount of water of the primer composition is preferably 150~1000 parts by weight to 100 parts by weight of urethane resin, more preferably 150~500 parts by weight. In that case, by making the blending amount of water satisfy the above-described range, the storage stability is enhanced in higher and a primer coating layer having a given film thickness and smoothness can be easily formed.

The blending amount of water includes water contained in an aqueous dispersion of urethane resin, water contained in an aqueous dispersion of polyester resin, and water contained in an aqueous sol of inorganic oxide particles.

Blending Amount of (E) Water-Soluble Organic Solvent

When water-soluble organic solvent (E-component) is used in accordance with this invention, it is preferable to use 30~700 parts by weight of water-soluble organic solvent to 100 parts by weight of urethane resin. More preferably, it is used in 50~700 parts by weight. Since the blending amount of the water-soluble organic solvent meets the above-described range, the wettability of the primer composition to an optical base material (specifically, a plastic lens) is improved, and is applicable to various kinds of plastic-made optical base materials. Further, since the blending amount of the water-soluble organic solvent meets the above-described range, the poor appearance such as running, etc. may be suppressed, the drying characteristics of the primer coating layer is improved, the impact resistance and abrasion resistance are also improved.

With respect to poor appearance of the primer coating layer such as running: there are two types of plastic lenses, one is a mono-focal lens (a distant vision lens), the other is a bi-focal lens for both distant and near vision equipped with a near vision lens (that is "small lens" (kodama in Japanese)) to the front of a mono-focal lens (a distant vision lens). Similar to the mono-focal lens, when the primer coating layer is formed on the face of the small lens of the bi-focal lens, there occurs running of the primer composition applied to periphery of the small lens projected from the mono-focal lens. However, in cases where the water-soluble organic solvent (E-component) is used in the primer composition, poor appearance caused by running on the periphery of the small lens is suppressed.

In order to improve the wettability of the primer composition and to form the primer coating layer having an excellent appearance and in order not to occur the decrease in the impact resistance and abrasion resistance, the weight ratio of E-component to 100 parts by weight of A-component is preferably 50~650 parts by weight and more preferably 70~600 parts by weight. The water-soluble organic solvent exhibiting most excellently the above-described effects is exemplified by propylene glycol-n-butyl ether, ethylene glycol-mono-butyl ether, diethylene glycol butyl ether or dipropylene glycol-n-propyl ether. Weight ratio of propylene glycol-n-butyl ether, ethylene glycol-mono-butyl ether, diethylene glycol butyl ether or dipropylene glycol-n-propyl ether to 100 parts by weight of urethane resin is most preferably 30~100 parts by weight. In such weight ration as described above, most excellent effect can be obtained. When propylene glycol-n-butyl ether, ethylene glycol-mono-butyl ether, diethylene glycol butyl ether or dipropylene glycol-n-propyl ether is used in a mixture with another water soluble organic solvent, the total weight thereof is preferably 70~600 parts by weight to 100 parts by weight of urethane resin.

The amount of E-component includes that of water-soluble organic solvent used as a dispersing medium for inorganic oxide fine particles of C-component.

Other Optional Components:

It is, further, preferable to add a leveling agent in the primer composition for an optical article used in this invention for the purpose of the improvement in the smoothness of the primer coating layer obtained. Known leveling agents may be used without limitation, and preferred examples include silicone series, fluorine series, acryl series, vinyl series, etc. The leveling agent may be added in such an amount that it exists preferably in 10~10000 ppm, more preferably in 50~5000 ppm in the primer composition.

Method for Preparing a Primer Composition for an Optical Article of this Invention:

The primer composition for an optical article of this invention can be prepared by mixing (A)-component, (B)-component, (C)-component and (D)-component, and (E)-component and other components, if necessary. The order of mixing each of these components is not specifically restricted, but mixing is carried out by known methods. According to one of most preferred embodiments of this invention, in order to improve the dispersion-stability of the inorganic oxide fine particles in urethane resin and to improve the storage stability of the primer composition obtained while suppressing whitening, it is preferable that aqueous dispersion of (A) polyurethane resin and aqueous dispersion of (B) polyester resin, in the above-described given blending amount, are mixed at a temperature of 10~40° C. for 30 mins.~48 hours to obtain a mixture, then the mixture thus obtained is mixed with aqueous sol or organic solvent sol of (C) inorganic oxide fine particles in the above-described given blending amount to obtain a mixture, and then the mixture thus obtained is mixed with remaining D-component at a temperature of 10~40° C. for 30 mins.~48 hours so as to amount to the above-described given blending amount to prepare the primer composition for an optical article.

The primer composition for an optical article of this invention can be prepared by mixing the above-described each of components in such a quantitative relationship that satisfies the above-described blending amounts, but the solid content of the primer composition for an optical article may be preferably from 3 to 35 weight % (That is to say, when the whole of the primer composition for an optical article is taken as 100 weight %, it is preferable that solid content is from 3 to 35 weight %). Since the concentration of the solid content of the primer composition for an optical article satisfies the above-described ranges, the control of the film thickness of the primer coating layer formed is made easy and the improvements in the impact resistance and the adhesion are made easy.

When the primer composition for an optical article is used for the improvement in the adhesion of an optical base material to a photochromic coating layer (that is, it is used for a first laminated article), the concentration of the solid content of the primer composition for an optical article may be preferably from 15 to 35 weight %. By setting the concentration of the solid content of the primer composition for an optical article within such range, the control of the film thickness of the primer coating layer is made easy and a first laminated article obtained exhibits excellent properties.

The concentration of the solid content of the primer composition for an optical article can be converted from the blending ratio of the primer composition for an optical article and can be obtained by concentrating and drying the primer composition.

Next, an optical base material using the above-described primer composition for an optical article is described:

Optical Base Material

In this invention, the primer composition for an optical article of this invention is used for the improvement in the impact resistance of an optical base material, specifically, plastic lens. Illustrative examples of a plastic lens material (resin) include polycarbonate-series resins, acrylic-or-methacrylic-series (hereinafter referred to as just "(meth)acrylic) resins, allyl-series resins, thiourethane-series resins, urethane-series resins and thioepoxy-series resins.

Photochromic Optical Base Material

The primer composition for an optical article used in this invention has excellent adhesion, specifically with (meth)acrylate-series resins, particularly, with (meth)acrylate-series resins formed by curing a composition comprising polyfunctional acrylate having three or more (meth)acrylate groups and di(meth)acrylate having alkylene glycol chain having 2~15 repeating units. Since such (meth)acrylate-series resins have a large free space, they become a (meth)acrylate-series resin having excellent photochromic properties (that is, a material for photochromic optical base material) when they contain a photochromic compound. The primer composition for an optical article of this invention can be suitably used for a photochromic optical base material comprising such (meth)acrylate-series resins.

Since (meth)acrylate-series resins formed by curing a composition comprising polyfunctional acrylate having three or more (meth)acrylate groups and di(meth)acrylate having alkylene glycol chain having 2~15 repeating units have a large free space as mentioned above, they can contain a great deal of photochromic compound. Accordingly, the primer composition for an optical article of this invention can be suitably used for an optical base material comprising a photochromic coating layer which is prepared by coating the optical base material with a photochromic curable composition comprising the di(meth)acrylate-containing composition and a photochromic compound. The primer composition for an optical article of this invention can be suitably used for an optical base material obtained by curing thereon a photochromic curable composition as it is.

In the following descriptions, the afore-mentioned photochromic curable compositions are divided into two groups according to its application as described below: The photochromic curable composition used for forming a photochromic coating layer by applying it on the optical base material and curing is taken as a "photochromic coating agent". And, the photochromic curable composition which is cured as it is to form a photochromic optical base material is taken as a "casting curable composition".

Illustrative examples of the afore-mentioned polyfunctional acrylate having three or more (meth)acrylate groups include trimethylolpropanetri(meth)acrylate, torimethylolpropanetriacrylate, tetramethylolmethanetri(meth)acrylate, tetramethylolmethanetriacrylate. Illustrative examples of the afore-mentioned di(meth)acrylate having alkylene glycol chain having 2~15 repeating units include polyethyleneglycol dimethacrylate having average molecular weight of 536, polytetramethyleneglycol dimethacrylate having average molecular weight of 736, polypropyleneglycol dimethacrylate having average molecular weight of 536, polyethyleneglycol diacrylate having average molecular weight of 258, polyethyleneglycol diacrylate having average molecular weight of 308, polyethyleneglycol diacrylate having average molecular weight of 522, polyethyleneglycol methacrylate having average molecular weight of 272, polyethyleneglycol methacrylate having average molecular weight of 536, 2,2-bis[4-acryloxy(polyethoxy)phenyl]propane, 2,2-bis[4-acryloyloxy(diethoxy)phenyl]propane and 2,2-bis[4-acryloyloxy(polyethoxy)phenyl]propane.

To a composition comprising polyfunctional acrylate having three or more (meth)acrylate groups and di(meth)acrylate having alkylene glycol chain having 2~15 repeating units, another polymerizable monomer may be added; for example (meth)acrylate such as glycidyl methacrylate, urethane acrylate, etc. may be added.

By combining such a polymerizable monomer with a photochromic compound, a photochromic coating agent or a casting curable composition can be obtained.

The photochromic compound is not particularly restricted and known compounds may be used. For example, photochromic compounds described in Japanese Patent Application Publication (Toku-kai-Hei) No. 2-28165, Japanese Patent Application Publication (Toku-kai-Sho) No. 62-288830, International Publication WO 94/22850, pamphlet, International Publication WO 96/14596, pamphlet, International Publication WO 01/60811, pamphlet, U.S. Pat. No. 4,913,544 and U.S. Pat. No. 5,623,005 may be used. The amount of the photochromic compound may be properly determined according to the application of the photochromic coating agent or casting curable composition.

Next, a photochromic optical base material prepared by using photochromic coating agent or casting curable composition is described:

A Photochromic Optical Base Material Using the Casting Curable Composition:

Such a photochromic optical base material can be produced by known methods. To the casting curable composition, additives such as antioxidant, radical capturing agent, ultraviolet rays stabilizer, ultraviolet rays absorbing agent, releasing agent, color protecting agent, antistatic agent, fluorescent dye, dye, pigment, perfume, plasticizer, silane coupling agent, photopolymerization initiator, thermal polymerization initiator, etc. may be added, if necessary. Such a casting curable composition is cast in a mold, for example a mold having a concave suitable for the shape of the desired optical base material and cured by known methods to produce a photochromic optical base material.

A Photochromic Optical Base Material Using the Photochromic Coating Agent:

Such a photochromic optical base material can be produced by known methods. Additives such as silicon-series or fluorine-series surfactant (leveling agent), antioxidant, radical capturing agent, ultraviolet rays stabilizer, ultraviolet rays absorbing agent, releasing agent, color protecting agent, antistatic agent, fluorescent dye, dye, pigment, perfume, plasticizer, silane coupling agent, photopolymerization initiator, thermal polymerization initiator, etc. may be added to the photochromic coating agent, if necessary.

An optical base material may have not a primer coating layer or may have a primer layer formed by known primer compositions such as, for example, the primer composition comprising moisture-curable polyurethane resin described in Patent Literature 5.

A photochromic coating layer formed by a photochromic coating agent may be formed by applying a photochromic coating agent on an optical base material on which is formed a primer coating layer to cure. While the method of curing the photochromic coating agent is not particularly restricted, a method may be preferably used for curing by irradiation with light such as ultraviolet rays, etc. using a photopolymerization initiator-added photochromic coating agent.

When the photochromic coating agent is cured by irradiation with light such as ultraviolet rays, etc., known light sources may be used without restriction and time for irradiation with light by using the light sources may be properly determined depending on the specific requirements for a photochromic coating layer such as film thickness, etc.

When the photochromic coating agent is applied on the optical base material on which the primer coating layer is formed, no pretreatment is particularly required, but the photochromic coating agent may be applied after the primer coating layer is cured (dried) and then cooled.

A method for applying the photochromic coating agent on the optical base material on which the primer coating layer is formed is not particularly restricted, but includes dip-coating, spin-coating, dip-spin-coating, etc. Among them, spin-coating method may be preferably adopted from the viewpoint of uniform of coating layer.

Next, a method for forming the primer coating layer of the primer composition for an optical article of this invention on the optical base material is described below:

Method for Forming the Primer Coating Layer

The primer composition for an optical article of this invention is applied on the optical base material and curing (drying) the primer composition to produce an optical article having a primer coating layer formed on the optical base material.

The primer coating layer formed of the primer composition for an optical article of this invention does not lower the optical characteristic of the optical base material, specifically those of a plastic lens. Therefore, the plastic lens on which is formed the primer coating layer may be used as an optical article as it is. Further, an optical article (laminate) having excellent impact resistance and abrasion resistance may be prepared by applying a hard coating composition comprising inorganic oxide fine particles and hydrolyzable group-containing organosilicon compound on the primer coating layer and curing to laminate a hard coating layer.

When the primer composition for an optical article of this invention is applied to the optical base material, it is preferable to carry out pretreatment with respect to the optical base material for the purpose of improvement in the adhesion. Illustrative examples of the pretreatments include the degreasing treatment by an organic solvent, chemical treatment by basic aqueous solution or acidic aqueous solution, polishing treatment by abrasive, plasma treatment by the use of atmospheric pressure plasma or low pressure plasma, corona discharge treatment, flame treatment or UV-ozone treatment, etc. Among them, the degreasing treatment by an organic solvent, alkali-treatment, plasma treatment, corona discharge treatment or UV-ozone treatment may be preferably used separately, or in combination from the view point of improvement in the adhesion of the optical base material to the primer coating layer.

A method for applying the primer composition for an optical article to the optical base material is not particularly restricted, but its illustrative example includes dip-coating, spin-coating, dip-spin-coating, etc. Among them, the dip-coating may be preferably adopted from the viewpoint of the productivity and uniform of coating layer.

The primer composition for an optical article applied on the optical base material by the above-described methods is dried in order to remove finally a solvent contained in the primer composition for an optical article. It is preferable to form the primer coating layer by applying the primer composition for an optical article on the optical base material, then after the completion of application heating the primer composition on the optical base material to remove a solvent. The heating temperature is not particularly restricted, but may be preferably the range of from the room temperature to 120° C., and more preferably the range of from the room temperature to 100° C. from the view point of the prevention of the deformation or change in color of the optical base material. The heating time is not particularly restricted, but may be preferably usually the range of from one (1) minute to one (1) hour, and specifically preferably 20 minutes and below from the view point of the productivity.

As afore mentioned, the primer composition for an optical article of this invention has uses for improvements in the impact resistance of the optical article and in the adhesion of the optical base material and the photochromic coating layer. There is a case where the preferred thickness of the primer coating layer formed of the primer composition is different depending on each of its applications. Firstly, a case where the primer coating layer is used for the improvement in the impact resistance is described below:

Primer Coating Layer Used for the Improvement in the Impact Resistance (Production of an Optical Article)

In the case of the use for the improvement in the impact resistance, the primer coating layer of the primer composition for an optical article of this invention is usually formed on the optical base material, and then a hard coating layer as detailed below is formed on the primer coating layer.

Figure 2:
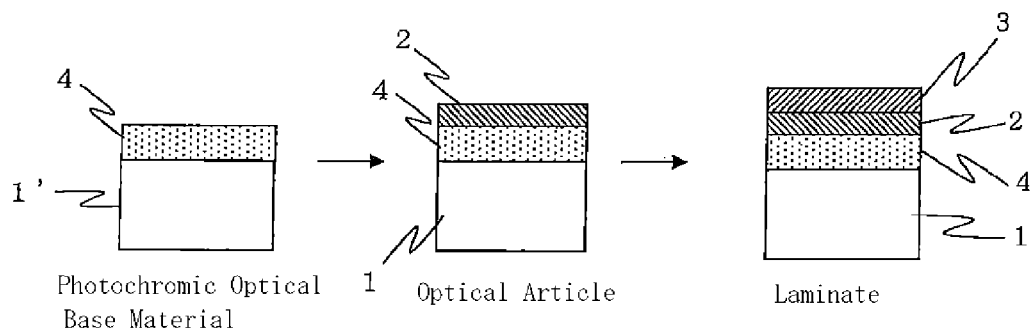
FIG. 2 is a flow diagram of another working embodiment for production of a laminate of this invention.

Flow sheets for the production of the optical articles are shown in FIG. 1 and FIG. 2. With reference to those Figs., the primer composition for an optical article of this invention is applied on the optical base material 1 and then dried to form the primer coating layer 2. When a photochromic optical base material 1' (that is prepared by forming a photochromic coating layer 4 on an optical base material) is used as an optical base material, the optical article is prepared in such a manner as shown in FIG. 2. In such a case, the primer coating layer 2 may be formed by applying the primer composition for an optical article of this invention on the photochromic coating layer 4 according to the above-described method, and drying.

For an optical article prepared in such a manner as described above, the hard coating layer 3 is usually formed on the primer coating layer 2. In such an optical article, the film thickness of the primer coating layer 2 may be preferably from 0.1 to 5.0 µm. Since the film thickness of the primer coating layer satisfies the above-described range, the impact resistance can be enhanced, and simultaneously, the problems of lowering of the abrasion resistance and occurrence of crack can be decreased when the hard coating layer is formed.

The Primer Coating Layer Used for the Improvement of the Adhesion of the Optical Base Material to the Photochromic Coating Layer (Production of a First and Second Laminated Articles)

The primer composition for an optical article of this invention can enhance the adhesion of the optical base material to the photochromic coating layer.

Figure 3:
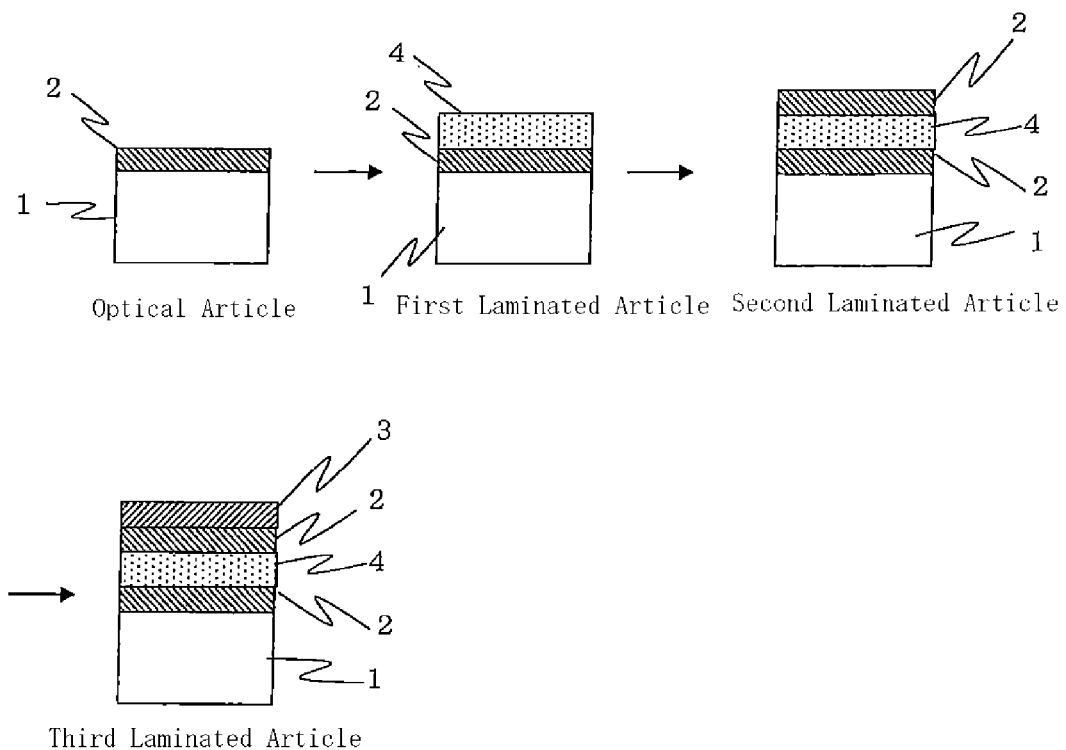
FIG. 3 is a flow diagram of a working embodiment for production of a third laminate of this invention.

A schematic block diagram for the process for production of a first laminated article obtained for this use is shown in FIG. 3. With reference to FIG. 1, the primer composition for an optical article of this invention is applied on the optical base material 1 in such a manner as described above and dried to form the primer coating layer 2' (production of an optical article). Then, the photochromic coating agent which is described with respect to the above-described photochromic optical base material is applied on the primer coating layer 2' to form the photochromic coating layer 4 in similar manner to that for production of the photochromic optical base material (production of a first laminated article).

The thickness of the primer coating layer 2' may be preferably from 0.5 µm to 20.0 µm, more preferably from 1.0 to 15.0 µm.

A first laminate article has excellent adhesion between the optical base material and the photochromic coating layer, and such a problem as occurrence of cracks with decrease in the impact resistance caused by the formation of the photochromic coating layer can be decreased.

The optical base material used may be a photochromic optical base material, but may be preferable a photochromic optical base material containing no photochromic compound in order to make the control of color tone easy. The thickness of the photochromic coating layer 4 is not particularly restricted, but may be preferable the range of 10~80 µm in order to exhibit excellent effects.

The first laminated article obtained in such a manner as described above may be used as it is. It is, however, preferable to form a primer coating layer for the improvement of the impact resistance when it is used for an eyeglass lens. A flow sheet of the laminated article (second laminated article) of such an embodiment is shown in FIG. 3.

With reference to FIG. 3, the second laminated article may be prepared by applying the primer composition for an optical article of this invention on the photochromic coating layer 4 of the first laminated article in such a manner as described above, and drying to form a primer coating layer 2. In this case, the thickness of the primer coating layer 2 may be preferably from 0.1~5.0 μm and below in order to improve the impact resistance.

As described above, the second laminated article on which the primer coating layer 2 is formed may be used for an eyeglass lens, etc. as they are. It is, however, more preferable to form a hard coating layer 3 on the primer coating layer 2, which is obtained by curing the coating composition comprising inorganic oxide fine particles and a hydrolyzable group-containing organosilicon compound (a third laminated article).

Next, the hard coating layer is described below:

Hard Coating Composition for Hard Coating Layer:

According to this invention, it is possible to laminate on the primer coating layer a hard coating layer obtained by curing the coating composition comprising inorganic oxide fine particles and a hydrolyzable group-containing organosilicon compound. As the inorganic oxide fine particles used for the hard coating layer, the afore-mentioned silica sol, inorganic oxide or complex inorganic oxide fine particles may be used without restriction. While the blending amount of the inorganic oxide fine particles may be properly determined depending on the types of the inorganic oxide, physical properties or objectives required for the hard coating layer finally obtained, in general, the blending amount of the inorganic oxide fine particles may be preferably determined so that the ratio of the inorganic oxide fine particles with respect to the hard coating layer finally obtained becomes 20~80 weight %, specifically 40~60 weight %. The weight of the hard coating layer may be obtained by weighting the weight of the solid content remaining after heating the coating composition at a temperature of 120° C. for three hours to remain.

The hydrolyzable group-containing organosilicon compound has a function as a binder for the inorganic oxide fine particles and forms a transparent cured product to be a matrix in the hard coating layer, and a polymerizable organosilicon compound may be used therefore. The organosilicon compound has an alkoxyl group as a functional group, and the afore-mentioned known hydrolyzable group-containing organosilicon compound may be used without limitation. The organosilicon compound may be used alone or in combination of two or more kinds. The organosilicon compound may be used in the form that at least a part thereof is hydrolyzed or in the form of partial condensate formed by condensation of its partial hydrolysate. In this invention, γ-glycidoxypropyltrimethoxysilane, γ-glycidoxypropylmethyldimethoxysilane, tetraethoxysilane, methyltriethoxysilane, 1,2-bis(triethoxysilyl)ethane or partial hydrolysate thereof or partial condensate thereof may be preferably used from the view point of adhesion with a plastic lens or capability of being crosslinked.

According to this invention, in order to prevent the crack of the hard coating layer and the lowering of the storage stability of the coating composition, the hydrolyzable group-containing organosilicon compound may be preferably used in 50 to 500 parts by weight, more preferably in 60 to 400 parts by weight, and specifically preferably in 70 to 300 parts by weight to 100 parts by weight of inorganic oxide fine particles. It may be also preferable that the hydrolyzable group-containing organosilicon compound is used so that the total amount of the hydrolyzable group-containing organosilicon compound and inorganic oxide fine particles exists in the hard coating composition in 15~50 weight %, preferably 20~40 weight %. The hydrolyzable group-containing organosilicon compound herein described is in such a state that an alkoxyl group contained is not hydrolyzed.

In the hard coating composition for forming the hard coating layer, the hydrolyzable group-containing organosilicon compound is hydrolyzed to form a hydrolysate, then the hydrolysate is polymerized and cured (polycondensation) in the form that it uptakes the inorganic oxide fine particles to form a cured product for a matrix, said cured product forming the hard coating layer comprising the matrix in which the inorganic oxide fine particles are dispersed closely. Therefore, water is required for acceleration of the hydrolysis of the hydrolyzable group-containing organosilicon compound in order to form the cured product.

The amount of such water may be 20~80 parts by weight, preferably in 20~65 parts by weight, and more preferably in 20~60 parts by weight to 100 parts by weight of total amount of the inorganic oxide fine particles and the hydrolyzable group-containing organosilicon compound. When the amount of water is too small, the hydrolysis of the alkoxy group contained in the hydrolyzable group-containing organosilicon compound does not progress sufficiently, and therefore the hardness of the hard coating layer obtained and the characteristics of the storage stability of the coating composition, etc. may be possibly lowered. On the other hand, when an excessive amount of water than necessary is used, it is difficult to form the hard coating layer having a uniform thickness, which adversely affects the optical characteristics of the optical base material on which the hard coating layer is formed.

The water used may be added in the form of acid aqueous solution; and for example, inorganic acid such as hydrochloric acid, sulfuric acid, nitric acid, phosphoric acid, etc. or organic acid such as acetic acid, propionic acid, etc. may be added in the form of aqueous solution thereof. Among them, hydrochloric acid or acetic acid may be preferably used from the view point of the storage stability and hydrolyzability of the hard coating composition. The concentration of the acid aqueous solution may be preferably 0.001~0.5N, specifically 0.01~0.1N. As previously mentioned, inorganic oxide fine particles may be possibly used in the form of dispersion (sol) formed by dispersing them in water. Therefore, the amount of the water contained in the hard coating composition for the hard coating layer is adjusted so that the total amount of the water contained in the aqueous dispersion of inorganic oxide fine particles and acid aqueous solution falls in the above-described range. For example, when the amount of the water contained in the dispersion of the inorganic oxide fine particles satisfies the above-described range of the amount of the water, no additional water is required. On the other hand, when the amount of the water contained in the dispersion of the inorganic oxide fine particles does not satisfy the above-described range of the amount of the water, additional water is necessary.

A curing catalyst for acceleration of hydrolysis of the hydrolyzable group-containing organosilicon compound may be added to the coating composition for the hard coating layer. As such a curing catalyst, known ones, for example, acetylacetonato complex, perchlorate, organometallic salt, various kinds of Lewis acids may be used. These may be used independently or in combination of two or more kinds.

Illustrative examples of acetylacetonato complex include aluminum acetylacetonato, lithium acetylacetonato, indium acetylacetonato, chromium acetylacetonato, nickel acetylacetonato, titanium acetylacetonato, iron acetylacetonato, zinc acetylacetonato, cobalt acetylacetonato, copper acetylacetonato, zirconium acetylacetonato, etc. Among them, aluminum acetylacetonato or titanium acetylacetonato may be preferable.

Illustrative examples of perchlorate include magnesium perchlorate, aluminum perchlorate, zinc perchlorate, ammonium perchlorate, etc.

Illustrative examples of organometallic salt include sodium acetate, zinc naphthenate, cobalt naphthenate, zinc octylate, etc.

Illustrative examples of Lewis acid include stannic chloride aluminum chloride, ferric chloride, titanium chloride, zinc chloride, antimony chloride, etc.

As a curing catalyst, acetylacetonato complex may be specifically preferable, from the view point that for the hard coating composition used for the hard coating layer, a hard coating layer having high abrasion resistance can be obtained at relatively lower temperatures for a short range of time. The acetylacetonato complex may preferably constitute 50 weight % and above, and specifically 70 weight % and above of a curing catalyst; it is most suitable that the whole amount of polymerization catalyst is an acetylacetonato complex.

The above-described curing catalyst may be preferably used in 1~15 parts by weight, specifically in 1~10 parts by weight to 100 parts by weight of the afore-mentioned hydrolyzable group-containing organosilicon compound from the view point that a hard cured film can be obtained.

An organic solvent may be added to the hard coating composition for the hard coating layer. Such an organic solvent is a solvent for the hydrolyzable group-containing organosilicon compound and is a dispersing medium for the inorganic oxide fine particles. Known organic solvents may be used as long as they have such functions and volatility at the same time. Illustrative examples of such organic solvents include alcohols such as methanol, ethanol, propanol, isopropanol, butanol, diacetone alcohol, etc.; lower alcohol esters of lower carboxylic acid such as methyl acetate, ethyl acetate, propyl acetate, etc.; ethers such as cellosolve, dioxane, ethylene glycol monoisopropyl ether, etc.; ketones such as acetone, methyl ethyl ketone, methylisobutyl ketone, acetylacetone, etc.; halogenated hydrocarbons such as methylene chloride, etc.; aromatic hydrocarbons such as benzene, toluene, xylene, etc. These organic solvents may be used independently or in combination of two or more kinds. Among these organic solvents, methanol, isopropanol, t-butyl alcohol, diacetone alcohol, ethylene glycol monoisopropyl ether or acetylacetone may be preferably used from the view points that they have compatibility with water added optionally and that when the coating composition is applied to be cured, they evaporate easily to form a smooth coating layer. As described above, a part of such organic solvents may be mixed previously with the inorganic oxide fine particles as a dispersing medium for the inorganic oxide fine particles.

The amount of use of the organic solvent is not specifically restricted, but the total amount thereof may be preferably 100~2500 parts by weight, specifically 140~150 parts by weight to 100 parts by weight of the afore-mentioned hydrolyzable group-containing organosilicon compound in order to obtain the storage stability and sufficient abrasion resistance. The amount of use of the organic solvent herein described is not an amount in case where the amount of alcohol produced at the time of hydrolysis of the hydrolyzable group-containing organosilicon compound is taken into consideration, but an amount in case where the hydrolyzable group-containing organosilicon compound is not hydrolyzed.

The hard coating composition for forming the hard coating layer may be produced by mixing the above-described components by means of known methods. Particularly, the hydrolyzable group-containing organosilicon compound may be preferably mixed with other components after the hydrolyzable group-containing organosilicon compound is completely hydrolyzed.

Method of Forming the Hard Coating Layer (Production of Laminate and Third Laminated Article)

According to this invention, the hard coating layer of the above-described coating composition may be formed on the optical article or second laminated article on which are previously formed the primer coating layer (a laminate and a third laminated article can be produced).

FIG. 1 and FIG. 2 show flow sheets in a case where the hard coating layer 3 is formed on the primer coating layer 2 of the optical article (process for producing a laminate). FIG. 3 shows a flow sheet in a case where the hard coating layer 3 is formed on the primer coating layer 2 of the second laminated article (process for producing a third laminated article).

According to this invention, the hard coating layer 3 may be formed by applying the hard coating composition onto the primer coating layer 2 formed on the optical article or a second laminated article and drying to cure. By forming the hard coating layer 3, a product having an excellent impact resistance and abrasion resistance can be produced.

According to this invention, when the hard coating composition for the hard coating layer is applied onto the primer coating layer 2 formed on the optical article or a second laminated article, a pretreatment is not specifically required, but the hard coating composition may be applied after the primer coating layer 2 is cured (dried) and cooled.

A method of applying the hard coating composition on the primer coating layer 2 is not specifically restricted, but a dip-coating method, spin-coating method, dip-spin-coating method, etc. may be adopted. Among them, a dip-coating method may be preferably adopted from the view point of productivity and uniform of the coating layer.

A solvent contained in the hard coating composition must be removed (dried) finally by heat-treating the coating composition applied on the primer coating layer 2. It is preferable to form the hard coating layer 3 by heating the coated film of the hard coating composition applied to remove a solvent. The heating temperature is not specifically restricted, but may be preferably in the range of 90~130° C., specifically preferably 90~110° C. from the view points of the adhesion, impact resistance and prevention of deformation or change in color of plastic lens by heating. The heating time is not specifically restricted, but may be preferable the range of one (1) hour to five (5) hours, specifically preferably the range of one (1) hour to three (3) hours from the view point of productivity.

The film thickness of the hard coating layer 3 formed in such a manner as described above may be preferably 1.0~4.0 μm. Since the film thickness of the hard coating layer satisfies the above-described range, a laminate having the excellent impact resistance and abrasion resistance can be obtained.

Since the primer composition for an optical article of this invention has high effect of the improvement in the impact resistance, it may be suitably applied to a laminate on which is formed a hard coating layer having Bayer ratio of 5.0 and above, preferably 5.5 and above.

Other Layers:

According to this invention, processings or secondary treatment such as antireflection treatment, antistatic treatment, etc. by vapor deposition of a thin film of inorganic oxide such as $SiO_2$, $TiO_2$, $ZrO_2$, etc. or by application of a thin film of an organic polymer etc. may be applied to a laminate or a third laminated article having the hard coating layer of the hard coating composition for the hard coating layer, if necessary.

EXAMPLES

This invention shall be described in more detail with reference to the following examples, but this invention shall not be restricted to these examples.

Each of components and plastic lenses (optical base material) used in examples are described below:

Plastic Lens (Diameter: 70 mm, Thickness: 2.0 mm)

Lens-A (thiourethane-series resin plastic lens: refractive index=1.60)

Lens-B (thiourethane-series resin plastic lens: refractive index=1.67)

Lens-C (thioepoxy-series resin plastic lens: refractive index=1.71)

Lens-D (thioepoxy-series resin plastic lens: refractive index=1.74)

Lens-E (polycarbonate resin plastic lens: refractive index=1.59)

The above-described lenses were used.

Photochromic Optical Base Materials Used:

Lens-F (a plastic lens having a methacrylic-series resin coating layer (photochromic coating layer) on the surface of the plastic lens)

Lens-G (a photochromic optical base material obtained by a casting method)

Method of Preparation of Lens-F 2,2-bis(4-acryloyloxypolyethylenglycolphenyl) propane having an average molecular weight of 776/polyethyleneglycol diacrylate (average molecular weight: 532)/trimethylolpropane trimethacrylate/polyester oligomer hexaacrylate/glycidyl methacrylate which were radically polymerizable monomers were mixed in a mixing proportion of 40 parts by weight/15 parts by weight/25 parts by weight/10 parts by weight/10 parts by weight to prepare a mixture of radical polymerizable monomers. Then, to 100 parts by weight of the mixture of radically polymerizable monomers thus prepared, 3 parts by weight of photochromic compound (I) illustrated by the following formula were added, and was subjected to ultrasonic dissolution carried out at a temperature of 70° C. for 30 minutes to prepare a polymerizable composition. After that, to the polymerizable composition thus obtained, 0.35 parts by weight of CGI1870 as a polymerization initiator (a mixture of 1-hydroxycyclohexylphenylketone and bis(2,6-dimethoxybenzoyl)-2,4,4-trimethyl-pentylphosphinoexide (weight ratio=3:7), 5 parts by weight of bis(1,2,2,6,6-pentmethyl-4-piperidyl) sebacate as a stabilizer, 3 parts by weight of triethyleneglycol-bis[3-(3-t-butyl-5-methyl-4-hydroxyphenyl)propionate] as a stabilizer, 7 parts by weight of γ-methacryloyloxypropyltrimethoxysilane as a silane coupling agent and 0.1 parts by weight of "L-7001"[(silicone-surfactant as a leveling agent (trade name; manufacture by Dow Corning Toray Co., Ltd.)) were added and mixed vigorously to prepare a photochromic curable composition (photochromic coating agent 1)).

A Photochromic Compound (1)

[chemical formula 1]

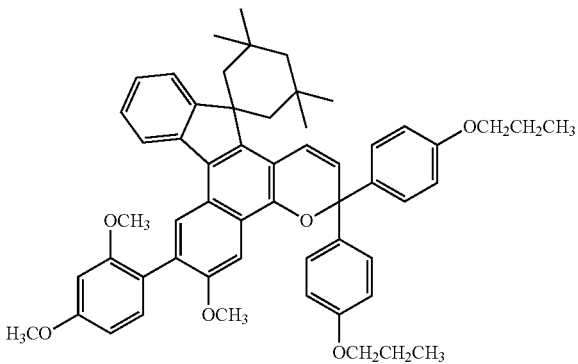

Lens B of the thickness 2.0 mm (thiourethane-series plastic lens; refractive index=1.67) was used as an optical base material. Lens B was degreased sufficiently by acetone, treated by 5% aqueous solution of sodium hydroxide of 50° C. for 4 minutes, rinsed by running water for 4 minutes, rinsed by distilled water of 40° C. for 4 minutes, and then dried at a temperature of 70° C. Then, 50 parts by weight of a moisture-curing type primer "Takeseal PFR402TP-4" (manufactured by Takebayashi Chemical Ind. Co., Ltd.) was mixed with 50 parts by weight of ethyl acetate to prepare a mixed liquid. To the mixed liquid thus prepared 0.03 parts by weight of leveling agent "FZ-2104" (trade name; manufacture by Dow Corning Toray Co., Ltd.) were added and stirred vigorously under nitrogen atmosphere to prepare liquid. The liquid thus obtained was used as primer coating liquid. The primer liquid was spin-coated on the surface of Lens B by means of a spin-coater "1H-DX2" (trade name; manufactured by MIKASA Co., Ltd.). Subsequently, Lens B thus treated was allowed to stand at a room temperature for 15 minutes to prepare a plastic lens having a primer coating layer of 7 μm in film thickness.

Thereafter, 1 g of the photochromic coating agent prepared in such a manner as described above was spin-coated on the surface of the above-described plastic lens having a primer coating layer (7 μm). The lens on the surface of which is coated with the coating layer of the photochromic coating agent was irradiated with light for 3 minutes in nitrogen gas atmosphere to cure the coating layer by the use of UV curing apparatus "F3000SQ" (trade name, manufactured by FUSION UV SYSTEMS) equipped with D valve, adjusted so that the output power at 405 nm on the surface of the lens is 150 mW/cm². Thereafter, it was subjected to heat treatment in a thermostat of 110° C. for 1 hour to form LENS-E having a photochromic coating layer. The film thickness of the photochromic coating layer to be obtained can be adjusted depending on the conditions of spin coating. In this invention, the film thickness of the photochromic coating layer was adjusted so as to be 40±1 μm.

Method of Preparation of Lens-G 43 parts by weight of polypropyleneglycol dimethacrylate having an average molecular weight of 328, 10 parts by weight of trimethylolpropane trimethacrylate, 5 parts by weight of methoxypolyethylene glycol methacrylate having an average molecular weight of 394, 16 parts by weight of polyethyleneglycol diacrylate (average molecular weight: 522, 1 part by weight of glycidyl methacrylate, 1 part by weight of α-methyl styrene dimer, and 25 parts by weight of urethane acrylate (manufactured by Daicel Corporation "EBECRYL" (trade name)) which were radically polymerizable monomers were mixed to prepare a polymerizable curing composition. Then, to 100 parts by weight of the polymerizable curing composition thus prepared, 0.1 parts by weight of bis(1,2,2,6,6-pentmethyl-4-piperidyl) sebacate, 0.03 parts by weight of photochromic compound (1), 1.0 part by weight of t-butylperoxineodecanate as a radical polymerization initiator, and 0.1 parts by weight of 2,2'-azobis(2,4-dimethyl valeronitril) as a radical polymerization initiator were added and mixed vigorously to prepare a photochromic curable composition. Then, the photochromic curable composition thus obtained was poured into a cast composed of a gasket made of a glass plate and ethylene-vinyl acetate copolymer and cast polymerization was carried out. In the cast polymerization, an air oven was used, the temperature of the air oven was gradually increased for 17 hours from 33° C. to 90° C., and then temperature of 90° C. was maintained for two hours. After the completion of the polymerization, the cast was taken out of the air oven and was allowed to cool down. After that, a cured product was taken out of the glass-made cast, then put into the oven, and heated at a temperature of 110° C. for three hours.

A-Component: Aqueous Dispersion of Urethane Resin:

U1: "SUPERFLEX420" (registered trade mark, manufactured by Dai-ichi Kogyou Seiyaku Co. Ltd., average particle diameter: 120 nm, elongation: 280%, Tg: −20° C., 100% modulus: 15N/mm$^2$, solid content (urethane resin) concentration: about 35 weight %, water: about 65 weight %, contains polycarbonate-derived skeleton, crosslinkable).

U2: "SUPERFLEX460" (registered trade mark, manufactured by Dai-ichi Kogyou Seiyaku Co. Ltd., average particle diameter: 100 nm, elongation: 750%, Tg: −25° C., 100% modulus: 2N/mm$^2$, solid content (urethane resin) concentration: about 38 weight %, water: about 62 weight %, contains polycarbonate-derived skeleton, crosslinkable).

U3: "EVAFANOL HA-50C" (registered trade mark, manufactured by NICCA CHEMICAL Co., Ltd., average particle diameter: 80 nm, elongation: 450%, Tg: −30° C., 100% modulus: 7N/mm$^2$, solid content (urethane resin) concentration: about 35 weight %, water: about 65 weight %, contains polycarbonate-derived skeleton, crosslinkable).

U4: "HYDRAN WLS-213" (registered trade mark, manufactured by DIC Corporation, average particle diameter: 120 nm, elongation: 400%, Tg: −30° C., 100% modulus: 6N/mm$^2$, solid content (urethane resin) concentration: about 35 weight %, water: about 65 weight %, contains polycarbonate-derived skeleton, uncrosslinkable).

U5: "Neorez R-9603" (trade name, commercially available from KUSUMOTO CHEMICALS, Ltd., average particle diameter: 70 nm, elongation: 10%, Tg: −10° C., solid content (urethane resin) concentration: about 33 weight %, water: about 53 weight %, contains polycarbonate-derived skeleton, uncrosslinkable).

Aqueous Dispersion of Urethane Resin not-Corresponding to A-Component (Aqueous Dispersion of Urethane Resin Containing No Polycarbonate-Derived Skeleton):

U6: "SUPERFLEX150" (registered trade mark, manufactured by Dai-ichi Kogyou Seiyaku Co. Ltd., average particle diameter: 150 nm, elongation: 330%, Tg: 30° C., solid content (urethane resin) concentration: about 30 weight % contains polyester-ether-derived skeleton, crosslinkable).

U7: "SUPERFLEX300" (registered trade mark, manufactured by Dai-ichi Kogyou Seiyaku Co. Ltd., average particle diameter: 150 nm, elongation: 1500%, Tg: −40° C., solid content (urethane resin) concentration: about 30 weight %, contains polyester-ether-derived skeleton, crosslinkable).

B-Component: Aqueous Dispersion of Polyester Resin:

P1: "VYLONAL MD-1930" (registered trade mark, manufactured by TOYOBO CO., LTD. Tg: −20° C., number average molecular weight: 20000, solid content (polyester resin) concentration: about 31 weight %, water: about 58 weight %, ethylene glycol mono-t-butyl ether: about 11 weight %)

P2: "VYLONAL MD-1985" (registered trade mark, manufactured by TOYOBO CO., Ltd. Tg: −20° C., number average molecular weight: 25000, solid content (polyester resin) concentration: about 27 weight %, water: about 64 weight %, ethylene glycol mono-n-butyl ether: about 9 weight %)

P3: "PESURESIN" (registered trade mark, manufactured by TAKAMATSU OIL & FAT CO., LTD., Tg: −20° C., number average molecular weight: 25000, solid content (polyester resin) concentration: about 25 weight %, water: about 75 weight %)

C-component: Sol of Inorganic Oxide Fine Particles:

SOL1: methanol dispersion sol of complex inorganic oxide fine particles comprising zirconium oxide: 11.7 weight %; tin oxide: 77.6 weight %; antimony oxide: 7.0 weight %; and silicon dioxide: 3.7 weight % (solid content concentration (concentration of complex inorganic oxide fine particles): 30 weight %, pH: 8.3)

SOL2: methanol dispersion sol of complex inorganic oxide fine particles comprising tin oxide: 12.0 weight %; titanium oxide: 61.3 weight %; zirconium oxide: 14.3 weight %; and silicon dioxide: 12.3 weight % (solid content concentration (concentration of complex inorganic oxide fine particles): 30 weight %, pH: 6.8).

SoL3: aqueous dispersion sol of complex inorganic oxide fine particles comprising tin oxide: 12.0 weight %; titanium oxide: 61.3 weight %; zirconium oxide: 14.3 weight %; and silicon dioxide: 12.3 weight % (solid content concentration (concentration of complex inorganic oxide fine particles): 25 weight %, pH: 8.5)

SOL4: methanol dispersion sol of complex inorganic oxide fine particles comprising tin oxide: 14.3 weight %; zirconium oxide: 74.6 weight %; and silicon dioxide: 11.1 weight % (solid content concentration (concentration of complex inorganic oxide fine particles): 38 weight %, pH: 7.5).

SOL5: aqueous dispersion sol of complex inorganic oxide fine particles comprising zirconium oxide: 74.6 weight %, tin oxide: 14.3 weight %; and silicon dioxide: 11.1 weight % (solid content concentration (concentration of complex inorganic oxide fine particles): 30 weight %, pH: 8.7)

SOL6: aqueous dispersion sol of complex inorganic oxide fine particles comprising tin oxide: 77.4 weight %; zirconium oxide: 12.9 weight %, and antimony oxide: 9.7 weight % (solid content concentration (concentration of complex inorganic oxide fine particles): 30 weight %, pH: 10.3)

E-Component: Water-Soluble Organic Solvent:

EG: ethylene glycol
EG1: ethylene glycol mono-isopropyl ether
DAA: diacetone alcohol
MeOH: methanol
TBA: t-butanol
DEB: diethylene glycol mono-butyl ether
DPNP: dipropylene glycol-n-propyl ether
PNB: propylene glycol-n-butyl ether
EMB: ethylene glycol mono-butyl ether Method of Preparation of Coating Composition for Hard Coating Layer:

Preparation of Hard Coating Composition-1:

77.9 g of γ-glycidoxypropyltrimethoxysilane and 23.5 g of tetraethoxysilane which are as an organic silicon compound, 30.8 g of t-butyl alcohol, 82.0 g of diacetone alcohol, 20.0 g of methanol which are as an organic solvent, and 0.3 g of silicon surfactant (manufactured by Dow Corning Toray Co., Ltd. "L-7001" (trade name)) were mixed to prepare a solution thereof. While stirring the solution thus prepared vigorously, a mixture of 52.0 g of water and 26 g of 0.05N hydrochloric acid was added to the solution, and after termination of the addition, stirring was continued for 20 hours, then 5.0 g of tris(2,4-pentanedionate)aluminum (III) were added to the solution, stirred for one hour, thereafter 182 g of methanol dispersion sol of complex inorganic oxide fine particles comprising zirconium oxide: 11.7 weight %; tin oxide: 77.6 weight %; antimony oxide: 7.0 weight %; and silicon dioxide: 3.7 weight % (solid content concentration (concentration of complex inorganic oxide fine particles): 40 weight %) were added and stirred for 24 hours to obtain the Hard Coating Composition-1.

Preparation of Hard Coating Composition-2:

88.3 g of γ-glycidoxypropyltrimethoxysilane as an organic silicon compound, 30.8 g of t-butyl alcohol and 102.0 g of diacetone alcohol which are as an organic solvent, and 0.3 g of silicon surfactant (manufactured by Dow Corning Toray Co., Ltd. "L-7001" (trade name)) were mixed together to prepare a solution thereof. While stirring the solution vigorously, a mixture of 52.0 g of water and 26 g of 0.05N hydrochloric acid was added to the solution, and after termination of the addition, stirring was continued for 20 hours. Then, 5.0 g of tris(2,4-pentanedionate)aluminum (III) were added to the solution, and stirred for one hour. Thereafter, 234 g of methanol dispersion sol of complex inorganic oxide fine particles comprising tin oxide: 12.0 weight %; titanium oxide: 61.3 weight %; zirconium oxide: 14.3 weight %; and silicon dioxide: 12.3 weight % (solid content concentration (concentration of complex inorganic oxide fine particles): 30 weight %, pH: 6.8) were added to the solution and stirred for 24 hours to obtain the Hard Coating Composition-2.

Preparation of Hard Coating Composition-3:

88.3 g of γ-glycidoxypropyltrimethoxysilane as an organosilicon compound, 30.8 g of t-butyl alcohol and 102.0 g of diacetone alcohol which are as an organic solvent, and 0.3 g of silicon surfactant (manufactured by Dow Corning Toray Co., Ltd. "L-7001" (trade name)) were mixed together to prepare a solution thereof. While stirring the solution vigorously, a mixture of 52.0 g of water and 26 g of 0.05N hydrochloric acid was added to the solution, and after termination of the addition, stirring was continued for 20 hours. Then, 5.0 g of tris(2,4-pentanedionate)aluminum (III) were added to the solution, and stirred for one hour. Thereafter, 234 g of methanol dispersion sol of complex inorganic oxide fine particles comprising titanium oxide: 78.6 weight %; zirconium oxide: 1.6 weight %, and silicon dioxide: 19.8 weight % (solid content concentration (concentration of complex inorganic oxide fine particles):30 weight %) were added to the solution and stirred for 24 hours to obtain the Hard Coating Composition-3.

Example 1

Preparation of Primer Composition-A:

45 g of "SUPERFLEX 420" (U1) as A-component, 20 g of "VYLONAL MD-1930" (P1) as B-component, 160 g of water and 0.3 g of "FZ2118" (manufactured by Dow Corning Toray Co., Ltd. (trade name)) were weighed and stirred at a temperature of 20~25° C. for one (1) hour to prepare a mixture. Then, while stirring the mixture thus obtain, 75 g of methanol dispersion sol of complex inorganic oxide fine particles comprising tin oxide: 12.0 weight %; titanium oxide: 61.3 weight %; zirconium oxide: 14.3 weight %; and silicon dioxide: 12.3 weight % (solid content concentration (concentration of complex inorganic oxide fine particles): 30 weight %)(SOL2) as C-component were added to the mixture, and stirred at a temperature of 20~25° C. for three (3) hours to obtain the Primer Composition-A of this invention (see: Table-1). Primer Composition-A was stable at 15° C. for six (6) months. This stability of Primer Composition-A is a value evaluated by a method in which the primer composition thus prepared is stored at a temperature of 15° C., and then the physical properties of the primer composition itself and the physical properties of primer coating layer after coating are evaluated on whether or not they are equivalent to initial values thereof. Blending amount is shown in Table-1.

In Table-1: The blending amounts of each of components are described as they are. The amount of the water contained in the aqueous dispersion of resin, and the amount of water-soluble organic solvent, and the amount of the water contained in the sol of inorganic oxide fine particles, and the amount of water-soluble organic solvent are not described in the columns of D-component (water) and E-component (water-soluble organic solvent) of Table-1. In the columns of D-component (water) and E-component (water-soluble organic solvent) of Table-1, the water contained in the aqueous dispersion of resin and in sol of resin, the water added in order to prepare the Primer Composition-A other than the water-soluble organic solvent, and the blending amount of the water-soluble organic solvent are described. The blending amounts of each of the components which are converted to a part by weigh of A-component, results of the storage stability and the refractive index of the coating film are shown in Table-2. With respect to a plurality of E-components, values obtained by conversion of the total amount thereof are shown in Table-2.

Formation of Primer Coating Layer and Hard Coating Layer: Production of Laminate:

Lens-A was used as an optical base material. Lens-A was degreased sufficiently by acetone, and rinsed by ultrasonic for five minutes with 10 weight % aqueous solution of sodium hydroxide. Then, Lens-A thus treated was coated with the Primer Composition-A by dip-coating at the pulling-up speed of 5 cm/min. and dried at a temperature of 80° C. for 10 minutes to form a primer coating layer having the refractive index of 1.66 and the film thickness of 1.2 μm (production of an optical article). Thereafter, Lens-A thus treated was cooled to room temperature, coated with the Hard Coating Composition-3 by dip-coating at the pulling-up speed of 15 cm/min. and cured at a temperature of 110° C. for two hours to obtain a plastic lens (laminate) having a hard coating layer 2.2 μm in film thickness formed on the afore-mentioned primer coating layer (film thickness: 1.2 μm).

Evaluations were carried out for the plastic lens having the primer coating layer and the hard coating layer with respect to each of the evaluation items shown in (1) to (6) described below. As a result, the plastic lens has evaluations in which appearance 1: ⊚, appearance 2: ⊚, steel wool abrasion resistance: A (1 kg), B (3 kg), adhesion: 100/100, boiling adhesion (five hours): 100/100, impact resistance: 225 g. Results obtained were summarized in Table-3.

Evaluation Items:

(1) Appearance-1

Evaluations of the appearance of the plastic lens having the primer coating layer were carried out according to a method in which the lens having these coating layers was irradiated with light of a high-pressure mercury-vapor lamp to throw its projected image onto a white paper; and observation evaluation was carried visually. Evaluation standards are shown below.
  ⊚: nonuniformity of coating layer is not observed.
  ○: no special problems, but defect due to lines on the order of 1~2 lines is observed.
  Δ: defect due to lines on the order of 4~9 lines is observed.
  X: defect due to lines of 10 or above or cissing-like pattern or both is observed; it is fatal defect in appearance.
  (2) Appearance-2
  A haze value of the plastic lens having the primer coating layer and that of the plastic lens before coating were measured by the use of a "Haze Meter NDH 5000" (manufactured by NIPPON DENSHOKU INDUSTRIES CO., LTD. (trade name)). The degree of cloud was evaluated by its difference between the both (Δ haze value). Evaluation standards are shown below:
  ⊚: Δ haze value 0.00~0.10
  ○: Δ haze value 0.11~0.15.
  Δ: Δ haze value 0.16~0.20
  X: Δ haze value 0.21 and above
  Δ haze value=(haze value of the plastic lens having the primer coating layer)−(haze value of the plastic lens before coating)
  (3) Steel Wool Abrasion Resistance:
  The surface of a plastic lens was rubbed back-and-forth 10 times with steel wool ("BONSTAR #0000", trade name, manufactured by Nihon Steel Wool Co., Ltd.) under a load of 1 kg and 3 kg to visually evaluate degree of scratches. Evaluation criteria are shown below.
  A: hardly scratched (a case where scratches less than 5 are visually observed)
  B: extremely slightly scratched (a case where scratches from 5 to less than 10 are visually observed)
  C: slightly scratched (a case where scratches from 10 to less than 20 are visually observed)
  D: clearly scratched (a case where scratches of 20 and above are visually observed)
  E: peeling of a hard coating layer occurs.
  (4) Adhesion:
  The adhesion of a primer coating layer and hard coating layer to a plastic lens was evaluated by a crosscut tape test according to JIS D-0202. That is to say: 100 squares were made by cutting the surface of the hard coating layer at intervals of about 1 mm crosswise. Then, a cellophane self-adhesive tape ("Cellotape" registered trade mark, manufactured by NICHIBAN CO., LTD.) was adhered tightly over the 100 squares; subsequently the cellophane self-adhesive tape was peeled of quickly in a direction at right angles from the surface. After the peeling, the number of squares in which the hard coating layer remained was measured.
  (5) Boiling Adhesion Test:
  A plastic lens as a test piece was immersed in boiled distilled water every one hour, and then it was taken out of the boiled distilled water. After wiping drops of water off the plastic lens, the plastic lens thus treated was allowed to stand at room temperature for one hour, thereafter, the adhesion was evaluated similarly to the adhesion test method described in above (4). As for a plastic lens maintaining the adhesion, such a test was carried out until the boiling time reaches five hours in total. Similarly to the adhesion test method described in above (4), number of squares remained was measured.
  (6) Impact Resistance:
  Steel balls weighting 16 g, 32 g, 50 g, 80 g, 95 g, 112 g, 138 g, 151 g, 174 g, 198 g and 225 g were dropped from the height of 127 cm to the middle of the plastic lens as a test piece in increasing order of weight to evaluate on whether or not the plastic lens was cracked. The results of evaluation were shown by maximum weight of the steel ball.

Examples 2~22

Preparation of Primer Compositions-B~S:
Primer Compositions-B~S were prepared in such a manner as that of Primer Composition-A, except that aqueous dispersion of urethane resin (A-component), aqueous dispersion of polyester resin (B-component), inorganic oxide fine particles (C-component), water (D-component), and water-soluble organic solvent (E-component) which are shown in Table-1 were used. Blending amounts of each component were shown in Table-1 and Table-2.
Production of Laminate and Evaluation:
Plastic lenses (laminates) having a primer coating layer and hard coating layer were produced in such a manner as that of Example 1 to evaluate them, except that the primer compositions (B~S), the hard coating compositions and plastic base materials shown in Table-2 respectively were used. Results of the evaluation were shown in Table-3.

Comparative Examples 1~8

Preparation of Primer Compositions-T~Y, AA, and AB:
Primer Compositions-T~Y, AA, AB were prepared in such a manner as that of Primer Composition-A, except that aqueous dispersions of urethane resin (A-component), aqueous dispersions of polyester resin (B-component), inorganic oxide fine particles (C-component), water (D-component) and water-soluble organic solvent (E-component) as shown in Table-1 respectively were used. Blending amounts of each component were shown in Table-1 and Table-2.
Production of Laminate and Evaluation:
Plastic lenses (laminates) having a primer coating layer and a hard coating layer were produced in such a manner as that of Example 1, except that the Primer Compositions (T~Y, AA, AB), the hard coating compositions and plastic base materials shown in Table-2 respectively were used to evaluate them. Results of evaluation were shown in Table-3.

TABLE 1

| Primer composition No. | A component | | Urethane resin not-contained in A-component | | B component | | C component | | D component | E component | | | |
|---|---|---|---|---|---|---|---|---|---|---|---|---|---|
| | Compound | Blending amount (g) | Compound | Blending amount (g) | Compound | Blending amount (g) | Compound | Blending amount (g) | Blending amount (g) | Compound | Blending amount (g) | Compound | Blending amount (g) |
| A | U1 | 45 | — | — | P1 | 20 | SOL2 | 75 | 160 | | | | |
| B | U1 | 45 | — | — | P2 | 23 | SOL2 | 75 | 157 | | | | |
| C | U1 | 45 | — | — | P3 | 24.8 | SOL2 | 75 | 155 | | | | |
| D | U1 | 33 | — | — | P3 | 37 | SOL2 | 75 | 155 | | | | |

TABLE 1-continued

| Primer composition No. | A component Compound | A component Blending amount (g) | Urethane resin not-contained in A-component Compound | Urethane resin not-contained in A-component Blending amount (g) | B component Compound | B component Blending amount (g) | C component Compound | C component Blending amount (g) | D component Blending amount (g) | E component Compound | E component Blending amount (g) | E component Compound | E component Blending amount (g) |
|---|---|---|---|---|---|---|---|---|---|---|---|---|---|
| E | U1 | 31.5 | — | — | P3 | 38.5 | SOL2 | 75 | 155 | | | | |
| F | U1 | 30.5 | — | — | P3 | 39.5 | SOL2 | 75 | 155 | | | | |
| G | U1 | 50 | — | — | P3 | 20 | SOL2 | 75 | 155 | | | | |
| H | U1 | 56 | — | — | P3 | 14 | SOL2 | 75 | 155 | | | | |
| I | U2 | 30 | — | — | P2 | 35 | SOL1 | 75 | 155 | | | | |
| J | U3 | 33 | — | — | P1 | 30 | SOL1 | 75 | 155 | | | | |
| K | U4 | 33 | — | — | P3 | 37 | SOL2 | 75 | 155 | | | | |
| L | U4 | 33 | — | — | P3 | 37 | SOL3 | 90 | 140 | | | | |
| M | U1 | 33 | — | — | P3 | 37 | SOL4 | 60 | 170 | | | | |
| N | U4 | 33 | — | — | P3 | 37 | SOL4 | 60 | 170 | | | | |
| O | U4 | 33 | — | — | P3 | 37 | SOL4 | 60 | 155 | EG | 10 | DAA | 5 |
| P | U3 | 33 | — | — | P2 | 35 | SOL4 | 60 | 155 | EG2 | 10 | TBA | 7 |
| Q | U4 | 43 | — | — | P3 | 47 | SOL4 | 40 | 170 | | | | |
| R | U4 | 28 | — | — | P3 | 32 | SOL4 | 70 | 155 | EG | 10 | DAA | 5 |
| S | U5 | 48 | — | — | P1 | 20 | SOL2 | 75 | 160 | | | | |
| T | U1 | 58 | — | — | P3 | 7 | SOL2 | 75 | 160 | | | | |
| U | U1 | 27 | — | — | P3 | 38 | SOL2 | 75 | 160 | | | | |
| V | U1 | 25 | — | — | P1 | 15 | SOL2 | 100 | 160 | | | | |
| W | U1 | 63 | — | — | P1 | 42 | SOL2 | 35 | 160 | | | | |
| X | — | — | U6 | 52.5 | P1 | 20 | SOL2 | 75 | 160 | | | | |
| Y | — | — | U7 | 52.5 | P1 | 20 | SOL2 | 75 | 160 | | | | |
| AA | U1 | 45 | U6 | 20 | — | — | SOL2 | 75 | 160 | | | | |
| AB | U1 | 45 | U7 | 20 | — | — | SOL2 | 75 | 160 | | | | |

TABLE 2

| Primer composition No. | A-component (part by weight) | Urethane resin not-contained in A-component (part by weight) | B-component (part by weight) | C-component (part by weight) | D-component (part by weight) | E-component (part by weight) | Storage stability | Refractive index of coated film |
|---|---|---|---|---|---|---|---|---|
| A | 100 | | 39 | 143 | 1275 | 347 | 6 months or more | 1.67 |
| B | 100 | | 39 | 143 | 1276 | 347 | 6 months or more | 1.67 |
| C | 100 | | 39 | 143 | 1288 | 333 | 6 months or more | 1.67 |
| D | 100 | | 80 | 195 | 1768 | 455 | 6 months or more | 1.68 |
| E | 100 | | 87 | 204 | 1854 | 476 | 6 months or more | 1.69 |
| F | 100 | | 93 | 211 | 1915 | 492 | 6 months or more | 1.69 |
| G | 100 | | 29 | 129 | 1157 | 300 | 6 months or more | 1.67 |
| H | 100 | | 18 | 115 | 1030 | 268 | 6 months or more | 1.67 |
| I | 100 | | 83 | 197 | 1719 | 488 | 6 months or more | 1.61 |
| J | 100 | | 81 | 195 | 1678 | 483 | 6 months or more | 1.61 |
| K | 100 | | 80 | 195 | 1768 | 455 | 6 months or more | 1.68 |
| L | 100 | | 80 | 195 | 2223 | — | 6 months or more | 1.68 |
| M | 100 | | 80 | 197 | 1898 | 322 | 6 months or more | 1.61 |
| N | 100 | | 80 | 197 | 1898 | 322 | 6 months or more | 1.61 |
| O | 100 | | 80 | 197 | 1768 | 409 | 6 months or more | 1.61 |
| P | 100 | | 82 | 197 | 1722 | 349 | 6 months or more | 1.61 |
| Q | 100 | | 78 | 101 | 1550 | 165 | 6 months or more | 1.57 |
| R | 100 | | 82 | 271 | 2012 | 545 | 6 months or more | 1.62 |
| S | 100 | | 39 | 142 | 1286 | 345 | 6 months or more | 1.67 |
| T | 100 | | 9 | 111 | 1000 | 259 | 6 months or more | 1.67 |
| U | 100 | | 101 | 238 | 2180 | 556 | 6 months or more | 1.69 |
| V | 100 | | 53 | 343 | 2114 | 820 | 6 months or more | 1.74 |
| W | 100 | | 59 | 48 | 1022 | 111 | 6 months or more | 1.58 |
| X | — | 100 | 39 | 143 | 1323 | 347 | 6 months or more | 1.67 |
| Y | — | 100 | 39 | 143 | 1323 | 347 | 6 months or more | 1.67 |
| AA | 100 | 38 | — | 143 | 1291 | 333 | 6 months or more | 1.67 |
| AB | 100 | 38 | — | 143 | 1291 | 333 | 6 months or more | 1.67 |

TABLE 3

| | Primer composition | Optical base material | Hard coating composition | Appearance 1 | Appearance 2 | Abrasion resistance 1 kg loading | Abrasion resistance 3 kg loading | Adhesion | Boiling adhesion test 1 Hour | 2 Hours | 3 Hours | 4 Hours | 5 Hours | Impact resistance |
|---|---|---|---|---|---|---|---|---|---|---|---|---|---|---|
| Example 1 | A | A | 3 | ⊚ | ⊚ | A | B | 100 | 100 | 100 | 100 | 100 | 100 | 225 g |
| Example 2 | A | B | 3 | ⊚ | ⊚ | A | B | 100 | 100 | 100 | 100 | 100 | 100 | 151 g |
| Example 3 | A | C | 3 | ⊚ | ⊚ | A | B | 100 | 100 | 100 | 100 | 100 | 100 | 138 g |
| Example 4 | A | D | 3 | ⊚ | ⊚ | A | B | 100 | 100 | 100 | 100 | 100 | 100 | 138 g |
| Example 5 | B | A | 3 | ⊚ | ⊚ | A | B | 100 | 100 | 100 | 100 | 100 | 100 | 225 g |
| Example 6 | C | A | 3 | ⊚ | ⊚ | A | B | 100 | 100 | 100 | 100 | 100 | 100 | 225 g |
| Example 7 | D | F | 1 | ⊚ | ⊚ | A | B | 100 | 100 | 100 | 100 | 100 | 100 | 225 g |
| Example 8 | E | B | 3 | ⊚ | ⊚ | A | B | 100 | 100 | 100 | 100 | 100 | 80 | 151 g |
| Example 9 | F | B | 3 | ⊚ | ⊚ | A | B | 100 | 100 | 100 | 100 | 90 | 50 | 174 g |
| Example 10 | G | B | 3 | ⊚ | ○ | A | B | 100 | 100 | 100 | 100 | 100 | 100 | 151 g |
| Example 11 | H | B | 3 | ⊚ | △ | A | B | 100 | 100 | 100 | 100 | 100 | 100 | 138 g |
| Example 12 | I | C | 2 | ⊚ | ⊚ | A | B | 100 | 100 | 100 | 100 | 100 | 100 | 138 g |
| Example 13 | J | D | 1 | ⊚ | ⊚ | A | B | 100 | 100 | 100 | 100 | 100 | 100 | 138 g |
| Example 14 | K | F | 1 | ⊚ | ⊚ | A | B | 100 | 100 | 100 | 100 | 100 | 100 | 225 g |
| Example 15 | L | F | 1 | ○ | ⊚ | A | B | 100 | 100 | 100 | 100 | 100 | 100 | 225 g |
| Example 16 | M | C | 2 | ⊚ | ⊚ | A | B | 100 | 100 | 100 | 100 | 100 | 100 | 138 g |
| Example 17 | N | C | 2 | ⊚ | ⊚ | A | B | 100 | 100 | 100 | 100 | 100 | 100 | 138 g |
| Example 18 | O | A | 2 | ⊚ | ⊚ | A | B | 100 | 100 | 100 | 100 | 100 | 100 | 225 g |
| Example 19 | P | A | 3 | ⊚ | ⊚ | A | B | 100 | 100 | 100 | 100 | 100 | 100 | 225 g |
| Example 20 | Q | B | 2 | ⊚ | ⊚ | A | B | 100 | 100 | 100 | 100 | 100 | 100 | 198 g |
| Example 21 | R | D | 1 | ⊚ | ⊚ | A | B | 100 | 100 | 100 | 100 | 100 | 100 | 112 g |
| Example 22 | S | A | 3 | ⊚ | ⊚ | A | B | 100 | 100 | 100 | 100 | 100 | 100 | 112 g |
| Comparative example 1 | T | A | 3 | ⊚ | X | A | B | 100 | 100 | 100 | 100 | 100 | 100 | 198 g |
| Comparative example 2 | U | A | 3 | ⊚ | ⊚ | A | C | 100 | 100 | 100 | 70 | 0 | — | 198 g |
| Comparative example 3 | V | A | 3 | ⊚ | ⊚ | A | B | 100 | 100 | 70 | — | — | — | 95 g |
| Comparative example 4 | W | A | 3 | ⊚ | ⊚ | A | D | 100 | 100 | 100 | 100 | 100 | 100 | 225 g |
| Comparative example 5 | X | A | 3 | ⊚ | ⊚ | A | B | 100 | 100 | 100 | 100 | 100 | 100 | 95 g |
| Comparative example 6 | Y | A | 3 | ⊚ | ⊚ | A | D | 100 | 100 | 100 | 100 | 100 | 100 | 80 g |
| Comparative example 7 | AA | A | 3 | ⊚ | X | A | B | 100 | 100 | 100 | 100 | 100 | 100 | 151 g |
| Comparative example 8 | AB | A | 3 | ⊚ | X | A | C | 100 | 100 | 100 | 100 | 100 | 100 | 138 g |

As apparent from Examples 1~22, when urethane resin having a polycarbonate-derived skeleton (A-component), polyester resin (B-component) and inorganic oxide fine particles are used in preferable proportions, a primer composition having excellent storage stability can be formed, and furthermore, a laminate having a primer coated film having excellent refractive index, appearance, adhesion, boiling adhesion, abrasion resistance and impact resistance can be obtained.

On the other hand, when the primer compositions (T~Y, AA, AB) as shown in Comparative Examples 1~8 were used, at least one physical properties in the storage stability of the primer composition, and refractive index, appearance, adhesion, boiling adhesion, abrasion resistance and impact resistance of the primer coated film obtained were insufficient.

Example 23

Preparation of Primer Composition-Z:

Primer Composition-Z was prepared in such a manner as that of Primer Composition-A, except that aqueous dispersion of urethane resin (A-component), polyester resin (B-component), inorganic oxide fine particles (C-component), water (D-component) and water-soluble organic solvent (E-component) which are shown in Table-3 respectively were used. Blending amounts of each component were shown in Table-4 and Table-5

TABLE 4

| Primer composition No. | A component Compound | A component Blending amount (g) | B component Compound | B component Blending amount (g) | C component Compound | C component Blending amount (g) | D component Blending amount (g) | E component Compound | E component Blending amount (g) | E component Compound | E component Blending amount (g) |
|---|---|---|---|---|---|---|---|---|---|---|---|
| Z | U1 | 45 | P1 | 20 | SOL2 | 75 | 0 | — | — | — | — |

TABLE 5

| Primer composition No. | A-component (part by weight) | B-component (part by weight) | C-component (part by weight) | D-component (part by weight) | E-component (part by weight) | Stability | Refractive index of coated film |
|---|---|---|---|---|---|---|---|
| Z | 100 | 39 | 143 | 259 | 333 | 6 months or above | 1.67 |

Production of First Laminated Article and Evaluation:

Lens-B was used as an optical base material. This plastic lens was degreased sufficiently with acetone, treated with 5% water solution of sodium hydroxide heated at 50° C. for four (4) minutes, rinsed with running water for four (4) minutes, rinsed with distilled water heated at 40° C. for four (4) minutes, and dried at a temperature of 70° C. Then, the Primer Composition-Z was spin-coated on the surface of Lens-B by means of a spin coater "1H-DX2" (trade name, manufactured by MIKASA Co., Ltd.). Lens-B thus treated was allowed to stand at room temperature for 15 minutes to prepare a plastic base material (optical article) having a primer coating layer 7 μm in film thickness.

Subsequently, about 1 g of the afore-mentioned photochromic coating agent (1) (photochromic coating agent used for preparation of Lens-E) was spin-coated on the surface of the optical base material (optical article) having the above-described coating layer. The lens the surface of which was coated with the coating film of the afore-mentioned photochromic coating agent was irradiated with light for 3 minutes in nitrogen gas atmosphere by the use of "F3000SQ" (trade name) equipped with D valve manufactured by FUSION UV SYSTEMS, adjusted so that the output power at 405 nm on the surface of the lens is 150 mW/cm$^2$ to cure the coating film and thereafter it was subjected to heat treatment in a thermostat of 110° C. for 1 hour to obtain a lens (first laminate) having a photochromic coating layer. The film thickness of the photochromic coating layer to be obtained can be controlled depending on the conditions of spin coating. In this invention, the film thickness of the photochromic coating layer was controlled so as to be 40±1 μm.

For the plastic lens having the primer coating layer and photochromic coating layer, evaluations were made for each of the afore-mentioned evaluation items (1), (2), (4) and (5). As a result, the plastic lens had the following physical properties: appearance 1: ⊚, appearance 2: ⊚, adhesion: 100/100, and boiling adhesion (five hours): 100/100. Results obtained were shown in Table-6.

Example 24

The primer coating layer (second laminated article) was formed on the plastic lens obtained by Example 23 (first laminated article) by the use of the primer composition-A and the Hard Coating Composition-3. Then, the hard coating layer was further formed on the primer coating layer formed to prepare a third laminated article. Results of the evaluations of the third laminated article were shown in Table-6.

TABLE 6

| | Primer composition No. | Optical base material | Hard coating composition | Appearance 1 | Appearance 2 | Abrasion resistance 1 kg loading | Abrasion resistance 3 kg loading | Adhesion | Boiling adhesion test 1 Hour | 2 Hours | 3 Hours | 4 Hours | 5 Hours | Impact resistance |
|---|---|---|---|---|---|---|---|---|---|---|---|---|---|---|
| Example 23 | Z | B | — | ⊚ | ⊚ | — | — | 100 | 100 | 100 | 100 | 100 | 100 | — |
| Example 24 | A | Lens prepared by Example 23 | 3 | ⊚ | ⊚ | A | B | 100 | 100 | 100 | 100 | 100 | 100 | 174 g |

As apparent from Example 23, in a case where a primer coating layer is formed by the use of the primer coating composition of this invention and a photochromic coating layer is laminated on the primer coating layer, a plastic lens having excellent appearance, adhesion and boiling adhesion can be obtained.

As apparent from Example 24, in a case where a first primer coating layer is formed on a plastic lens by using the primer coating composition of this invention and a photochromic coating layer is laminated on the first primer coating layer to prepare a lens having the first primer coating layer and the photochromic coating layer in that order, and further a second primer coating layer is formed on the photochromic coating layer and a hard coating layer is formed on the second primer coating layer, a plastic lens having excellent appearance, adhesion, boiling adhesion, abrasion resistance and impact resistance can be obtained.

Example 25~44

Preparation of Primer Compositions-AC~AI

Primer Compositions-(AC~AI) were prepared in such a manner as that of Primer Composition-A, except that aqueous dispersion of urethane resin (A-component), aqueous dispersion of polyester resin (B-component), inorganic oxide fine particles (C-component), water (D-component) and water-soluble organic solvent (E-component) which are shown in Table-7 respectively were used. Blending amounts of each component were shown in Table-7 and Table-8.

Production of Laminate and Evaluation:

Plastic lenses (laminates) having a primer coating layer and a hard coating layer were produced in such a manner as that of Example 1, except that the Primer Compositions- (AC~AI), the hard coating compositions and optical base materials shown in Table-8 respectively were used to evaluate them in such a manner as that of Example 1. Results of evaluations were shown in Table-9.

Preparation of Primer Composition-AJ

Primer Composition-AJ (not-containing A-component) was prepared in such a manner as that of Primer Composition-A, except that aqueous dispersion of polyester resin (B-component), inorganic oxide fine particles (C-component), water (D-component) and water-soluble organic solvent (E-component) which are shown in Table-7 respectively were used. Blending amounts of each component were shown in Table-7 and Table-8. Since the Primer Composition-AJ does not contain aqueous dispersion of urethane resin (A-component), the blending amounts shown in Table-8 are those which are converted to 100 parts by weight of aqueous dispersion of polyester resin (B-component).

Production of Laminate and Evaluation:

Plastic lenses (laminates) having a primer coating layer and a hard coating layer were produced in such a manner as that of Example 1, except that the Primer Composition-AJ, the hard coating compositions and optical base materials shown in Table-8 respectively were used to evaluate them in such a manner as that of Example. Results obtained were shown in Table-9.

TABLE 7

| Primer composition No. | A component Compound | A component Blending amount (g) | Urethane resin not-contained in A component Compound | Urethane resin not-contained in A component Blending amount (g) | B component Compound | B component Blending amount (g) | C component Compound | C component Blending amount (g) | D component Blending amount (g) | E component Compound | E component Blending amount (g) | E component Compound | E component Blending amount (g) |
|---|---|---|---|---|---|---|---|---|---|---|---|---|---|
| AC | U1 | 50 | — | — | P3 | 53 | SOL5 | 102 | 86 | DEB | 9 | | |
| AD | U1 | 50 | — | — | P3 | 53 | SOL5 | 102 | 86 | DPNP | 9 | | |
| AE | U1 | 50 | — | — | P3 | 53 | SOL5 | 102 | 86 | PNB | 9 | | |
| AF | U1 | 50 | — | — | P3 | 53 | SOL5 | 102 | 86 | EMB | 9 | | |
| AG | U1 | 50 | — | — | P3 | 53 | SOL5 | 102 | 86 | MeOH | 9 | | |
| AH | U1 | 50 | — | — | P3 | 53 | SOL6 | 102 | 86 | PNB | 9 | | |
| AI | U1 | 50 | — | — | P3 | 53 | SOL1 | 102 | 86 | PNB | 9 | | |
| AJ | — | — | — | — | P3 | 112 | SOL5 | 93 | 86 | PNB | 9 | | |

TABLE 8

| Primer composition No. | A component (part by weight) | Urethane resin not-contained in A-component (part by weight) | B component (part by weight) | C component (part by weight) | D component (part by weight) | E component (part by weight) | Storage stability | Refractive index of coated film |
|---|---|---|---|---|---|---|---|---|
| AC | 100 | — | 76 | 175 | 1312 | 51 | 6 months or more | 1.59 |
| AD | 100 | — | 76 | 175 | 1312 | 51 | 6 months or more | 1.59 |
| AE | 100 | — | 76 | 175 | 1312 | 51 | 6 months or more | 1.59 |
| AF | 100 | — | 76 | 175 | 1312 | 51 | 6 months or more | 1.59 |
| AG | 100 | — | 76 | 175 | 1312 | 51 | 6 months or more | 1.59 |
| AH | 100 | — | 76 | 175 | 1312 | 51 | 6 months or more | 1.59 |
| AI | 100 | — | 80 | 197 | 1820 | 400 | 6 months or more | 1.59 |
| AJ | — | — | 100* | 100* | 840* | 32* | 6 months or more | 1.59 |

*Blending amount wthen B compount is 100 parts by weight.

TABLE 9

| | Primer composition | Optical base material | Hard coating composition | Appearance 1 | Appearance 2 | Abrasion resistance 1 kg loading | Abrasion resistance 3 kg loading | Adhesion | Boiling adhesion test 1 Hour | 2 Hours | 3 Hours | 4 Hours | 5 Hours | Impact resistance |
|---|---|---|---|---|---|---|---|---|---|---|---|---|---|---|
| Example 25 | AC | A | 1 | ⊚ | ⊚ | A | B | 100 | 100 | 100 | 100 | 100 | 100 | 225 g |
| Example 26 | AD | A | 1 | ⊚ | ⊚ | A | B | 100 | 100 | 100 | 100 | 100 | 100 | 225 g |
| Example 27 | AE | A | 1 | ⊚ | ⊚ | A | B | 100 | 100 | 100 | 100 | 100 | 100 | 225 g |
| Example 28 | AE | B | 1 | ⊚ | ⊚ | A | B | 100 | 100 | 100 | 100 | 100 | 100 | 151 g |
| Example 29 | AE | C | 1 | ⊚ | ⊚ | A | B | 100 | 100 | 100 | 100 | 100 | 100 | 138 g |
| Example 30 | AE | D | 1 | ⊚ | ⊚ | A | B | 100 | 100 | 100 | 100 | 100 | 100 | 138 g |
| Example 31 | AE | G | 1 | ⊚ | ⊚ | A | B | 100 | 100 | 100 | 100 | 100 | 100 | 151 g |
| Example 32 | AF | A | 1 | ⊚ | ⊚ | A | B | 100 | 100 | 100 | 100 | 100 | 100 | 225 g |
| Example 33 | AG | A | 1 | ⊚ | ⊚ | A | B | 100 | 100 | 100 | 100 | 100 | 100 | 225 g |
| Example 34 | AH | A | 1 | ⊚ | ⊚ | A | B | 100 | 100 | 100 | 100 | 100 | 100 | 225 g |
| Example 35 | AI | A | 1 | ⊚ | ⊚ | A | B | 100 | 100 | 100 | 100 | 100 | 100 | 138 g |
| Example 36 | D | E | 1 | ⊚ | ⊚ | A | B | 100 | 100 | 100 | 100 | 100 | 100 | 225 g |
| Example 37 | J | E | 1 | ⊚ | ⊚ | A | B | 100 | 100 | 100 | 100 | 100 | 100 | 225 g |
| Example 38 | K | E | 1 | ⊚ | ⊚ | A | B | 100 | 100 | 100 | 100 | 100 | 100 | 225 g |
| Example 39 | L | E | 1 | ○ | ⊚ | A | B | 100 | 100 | 100 | 100 | 100 | 100 | 225 g |
| Example 40 | M | E | 1 | ⊚ | ⊚ | A | B | 100 | 100 | 100 | 100 | 100 | 100 | 225 g |

TABLE 9-continued

| | Primer composition | Optical base material | Hard coating composition | Appearance 1 | Appearance 2 | Abrasion resistance 1 kg loading | Abrasion resistance 3 kg loading | Adhesion | Boiling adhesion test 1 Hour | 2 Hours | 3 Hours | 4 Hours | 5 Hours | Impact resistance |
|---|---|---|---|---|---|---|---|---|---|---|---|---|---|---|
| Example 41 | N | E | 1 | ◉ | ◉ | A | B | 100 | 100 | 100 | 100 | 100 | 100 | 225 g |
| Example 42 | O | E | 1 | ◉ | ◉ | A | B | 100 | 100 | 100 | 100 | 100 | 100 | 225 g |
| Example 43 | P | E | 1 | ◉ | ◉ | A | B | 100 | 100 | 100 | 100 | 100 | 100 | 225 g |
| Example 44 | AE | E | 1 | ◉ | ◉ | A | B | 100 | 100 | 100 | 100 | 100 | 100 | 225 g |
| Comparative Example 9 | AJ | E | 1 | ◉ | ◉ | A | B | 100 | 50 | | | | | 225 g |

Examples 45~83

The film-forming properties of the primer composition of this invention with respect to a bi-focal lens were evaluated by the use of bi-focal lenses described below:
Bi-Focal Lens (Diameter: 70 mm, Thickness: 1.7 mm, Maximum Thickness of Small Lens (Kodama in Japanese): 0.7 mm):
Lens-H (thiourethane-series resin-made plastic lens same as Lens-A; refractive index=1.60; refractive index of small lens (kodama in Japanese)=1.60)
Lens-I (thiourethane-series resin-made plastic lens same as Lens-B; refractive index=1.67; refractive index of small lens (kodama in Japanese)=1.67)
Lens-J (thioepoxy-series resin-made plastic lens same as Lens-C; refractive index=1.71; refractive index of small lens (kodama in Japanese)=1.71)
Lens-K (thioepoxy-series resin-made plastic lens same as Lens-D; refractive index=1.74; refractive index of small lens (kodama in Japanese)=1.74)
Lens-L (polycarbonate resin-made plastic lens same as Lens-E; refractive index=1.59; refractive index of small lens (kodama in Japanese)=1.59)
Lens-M (integrally-molded lens by the use of the photochromic curable composition used for the production of the above-described Lens-G)

These bi-focal lenses are made by a cast-polymerization method in which polymerizable monomers for each lens were poured into a glass-made cast in which the shape of the small lens (kodama in Japanese) is carved and cured to integrally-mold a distant vision lens and a near vision small lens (kodama in Japanese).

Appearances on running when coating the surface of each optical base material used with each primer composition prepared in such a manner as described above were studied.

Appearance 3

Figure 4:
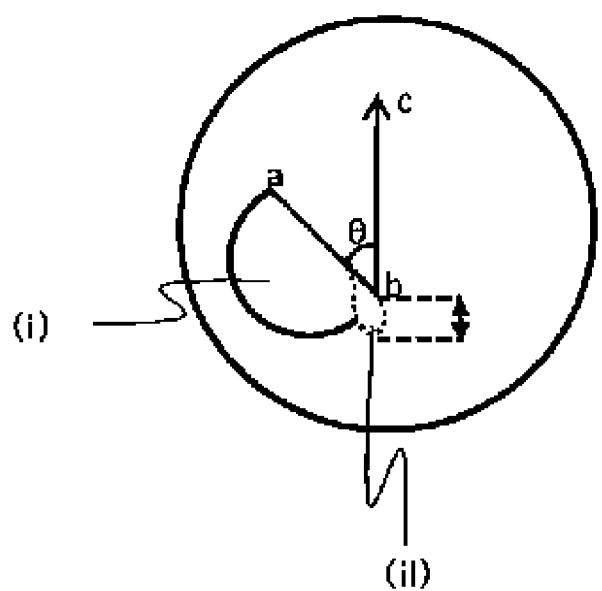
FIG. 4 is a schematic diagram showing a method of evaluation of film-forming properties (appearance 3) of s primer composition of this invention to a bifocal lens.

Bi-focal lenses were dip-coated with the primer composition and the film-forming properties of the primer composition on the bi-focal lenses were evaluated. As shown in FIG. 4, in the dip-coating, the bio-focal lens was pulled up from a dipping cell so that the angle (θ) formed between the side a-b which is a straight line of the small lens (kodama in Japanese) (i) of the bi-focal lens and the direction of pulling-up of the lens is 45 degrees. Evaluations were carried out by measuring the length of the running of the primer composition from the small lens (kodama in Japanese) shown in FIG. 4 to evaluate. Evaluation standards are shown below.

◉: length of running is 0 mm or above and less than 1 mm.
○: no special problems in appearance, but length of running of 1 mm or above and less than 3 mm is observed.
X: length of running of 3 mm or above is observed; it is fatal defect in appearance.

Results obtained were shown in Table-10.

TABLE 10

| | Primer composition | Optical base material | Appearance 3 |
|---|---|---|---|
| Example 45 | A | H | ○ |
| Example 46 | A | I | ○ |
| Example 47 | A | J | ○ |
| Example 48 | A | K | ○ |
| Example 49 | B | H | ○ |
| Example 50 | C | H | ○ |
| Example 51 | E | I | ○ |
| Example 52 | F | I | ○ |
| Example 53 | G | I | ○ |
| Example 54 | H | I | ○ |
| Example 55 | I | J | ○ |
| Example 56 | J | K | ○ |
| Example 57 | M | J | ○ |
| Example 58 | N | J | ○ |
| Example 59 | O | H | ○ |
| Example 60 | P | H | ○ |
| Example 61 | Q | I | ○ |
| Example 62 | R | K | ○ |
| Example 63 | S | H | ○ |
| Example 64 | AC | H | ◉ |
| Example 65 | AD | H | ◉ |
| Example 66 | AE | H | ◉ |
| Example 67 | AE | I | ◉ |
| Example 68 | AE | J | ◉ |
| Example 69 | AE | K | ◉ |
| Example 70 | AE | M | ◉ |
| Example 71 | AF | H | ◉ |
| Example 72 | AG | H | ○ |
| Example 73 | AH | H | ◉ |
| Example 74 | AI | H | ◉ |
| Example 75 | D | L | ○ |
| Example 76 | J | L | ○ |
| Example 77 | K | L | ○ |
| Example 78 | L | L | ○ |
| Example 79 | M | L | ○ |
| Example 80 | N | L | ○ |
| Example 81 | O | L | ○ |
| Example 82 | P | L | ○ |
| Example 83 | AE | L | ◉ |

It is evident from the results shown in Table-10 that when a water-soluble organic solvent (E-component) is used in the primer composition of this invention, excellent film properties can be obtained and very excellent film properties for a bi-focal lens can be obtained specifically by the use of diethylene glycol mono-butyl ether, dipropylene glycol-n-propyl ether, propylene glycol-n-butyl ether or ethylene glycol mono-butyl ether.

The invention claimed is:
1. A primer composition for an optical article comprising;
(A) an aqueous dispersion of urethane resin having a polycarbonate-derived skeleton (A-component);

(B) a polyester resin prepared by polycondensation of polybasic acid and polyhydric alcohol and containing no urethane bond (—NHCOO—) in its molecule (B-component);

(C) inorganic oxide fine particles (C-component); and (D) water (D-component), characterized in that to 100 parts by weight of A-component, B-component is 10~95 parts by weight, C-component is 70~300 parts by weight, and D-component is 150~2300 parts by weight.

2. The primer composition for an optical article as claimed in claim 1, wherein said urethane resin having a polycarbonate-derived skeleton has
an elongation from 200~1000%.

3. The primer composition for an optical article as claimed in claim 1 further comprising (E) water-soluble organic solvent (E-component).

4. The primer composition for an optical article as claimed in claim 3, wherein the blending amount of E-component is 30~700 parts by weight to 100 parts by weight of A-component.

5. The primer composition for an optical article as claimed in claim 3, characterized in that said (E) water-soluble organic solvent (E-component) comprises at least one selected from the group consisting of diethylene glycol mono-butyl ether, dipropylene glycol-n-propyl ether, propylene glycol-n-butyl ether and ethylene glycol mono-butyl ether.

6. The primer composition for an optical article as claimed in claim 5, wherein the blending amount of E-component is 30~700 parts by weight to 100 parts by weight of A-component.

7. An optical article having a primer coating layer obtained by curing the primer composition for an optical article as claimed in claim 1 on an optical base material.

8. The optical article of claim 7, further comprising a hard coating layer obtained by applying a hard coating composition comprising the inorganic oxide fine particles and the hydrolyzable group-containing organosilicon compound and curing the hard coating composition to thereby form a laminate.

9. An optical article as claimed in claim 7, wherein said optical base material is a photochromic optical base material.

10. An optical article as claimed in claim 9, wherein said photochromic optical base material comprises on the optical base material a photochromic coating layer obtained by applying a curable composition comprising a photochromic composition and curing, and on said photochromic coating layer a primer coating layer of the primer composition.

11. The optical article of claim 10, further comprising a hard coating layer obtained by applying a hard coating composition comprising the inorganic oxide fine particles and the hydrolyzable group-containing organosilicon compound and curing the hard coating composition to thereby form a laminate.

12. The optical article as claimed in claim 9, further comprising on the optical base material a photochromic coating layer obtained by applying a curable composition comprising a photochromic composition and curing, where the primer coating layer in disposed on said photochromic coating layer, and where said primer coating layer composition includes a water-soluble organic solvent in an amount from 30~700 parts by weight to 100 parts by weight of the aqueous dispersion.

13. The optical article of claim 9, further comprising a hard coating layer obtained by applying a hard coating composition comprising the inorganic oxide fine particles and the hydrolyzable group-containing organosilicon compound and curing the hard coating composition to thereby form a laminate.

14. An optical article including an optical base and a primer coating layer formed of the primer coating composition of claim 1, and having on said primer coating layer a photochromic coating layer obtained by curing a curable composition comprising a photochromic compound.

15. The optical article of claim 14 further including a hard coating layer obtained by curing a hard coating composition comprising the inorganic oxide fine particles and the hydrolyzable group-containing organosilicon compound.

16. An optical article comprising on the photochromic coating layer of the optical article as claimed in claim 14, wherein said urethane resin having a polycarbonate-derived skeleton has an elongation from 200~1000%.

17. The optical article of claim 14, where the primer coating composition further comprises a water-soluble organic solvent.

18. The optical article of claim 17, where the primer coating composition is characterized in that said water-soluble organic solvent comprises at least one selected from the group consisting of diethylene glycol mono-butyl ether, dipropylene glycol-n-propyl ether, propylene glycol-n-butyl ether, and ethylene glycol mono-butyl ether.

19. The optical article of claim 17, where the primer coating composition includes 30~700 parts by weight water-soluble organic solvent per 100 parts by weight of the aqueous dispersion.

20. An optical article having a primer coating layer obtained by curing the primer composition for an optical article as claimed in claim 2 on an optical base material.

21. An optical article having on the optical base material the primer coating layer formed of the primer coating composition for the optical article as claimed in claim 2, and having on said primer coating layer a photochromic coating layer obtained by curing the curable composition comprising a photochromic compound.

22. An optical article having a primer coating layer obtained by curing the primer composition for an optical article as claimed in claim 3 on an optical base material.

23. An optical article having on the optical base material the primer coating layer formed of the primer coating composition for the optical article as claimed in claim 3, and having on said primer coating layer a photochromic coating layer obtained by curing the curable composition comprising a photochromic compound.

24. An optical article having a primer coating layer obtained by curing the primer composition for an optical article as claimed in claim 5 on an optical base material.

25. An optical article having on the optical base material the primer coating layer formed of the primer coating composition for the optical article as claimed in claim 5, and having on said primer coating layer a photochromic coating layer obtained by curing the curable composition comprising a photochromic compound.

26. An optical article having a primer coating layer obtained by curing the primer composition for an optical article as claimed in claim 4 on an optical base material.

27. An optical article having on the optical base material the primer coating layer formed of the primer coating composition for the optical article as claimed in claim 4, and having on said primer coating layer a photochromic coating layer obtained by curing the curable composition comprising a photochromic compound.

* * * * *